US008722993B2

(12) United States Patent
Lowe et al.

(10) Patent No.: US 8,722,993 B2
(45) Date of Patent: May 13, 2014

(54) METHODS AND COMPOSITIONS FOR PRODUCTION OF MAIZE LINES WITH INCREASED TRANSFORMABILITY

(75) Inventors: Brenda A. Lowe, Mystic, CT (US); Paul S. Chomet, Mystic, CT (US)

(73) Assignee: Monsanto Technology LLC, St. Louis, MO (US)

( * ) Notice: Subject to any disclaimer, the term of this patent is extended or adjusted under 35 U.S.C. 154(b) by 0 days.

(21) Appl. No.: 12/778,889

(22) Filed: May 12, 2010

(65) Prior Publication Data

US 2010/0287653 A1 Nov. 11, 2010

Related U.S. Application Data

(62) Division of application No. 10/455,229, filed on Jun. 5, 2003, now Pat. No. 7,759,545.

(60) Provisional application No. 60/386,522, filed on Jun. 6, 2002.

(51) Int. Cl.
*A01H 5/10* (2006.01)
*A01H 5/00* (2006.01)
*A01H 1/02* (2006.01)

(52) U.S. Cl.
USPC .................. 800/320.1; 800/260; 800/275

(58) Field of Classification Search
USPC .............................. 800/260, 320.1
See application file for complete search history.

(56) References Cited

U.S. PATENT DOCUMENTS

| 5,641,664 | A | 6/1997 | D'Halluin et al. | 435/172.3 |
|---|---|---|---|---|
| 5,981,832 | A | 11/1999 | Johnson | 800/267 |
| 6,331,660 | B1 | 12/2001 | Chomet et al. | 800/278 |
| 6,362,403 | B1 * | 3/2002 | Pfund | 800/320.1 |
| 6,399,855 | B1 | 6/2002 | Beavis | 800/266 |
| 7,022,894 | B2 | 4/2006 | Ranch et al. | 800/268 |
| 7,759,545 | B2 * | 7/2010 | Lowe et al. | 800/275 |
| 2006/0101540 | A1 | 5/2006 | Ranch et al. | 800/278 |

FOREIGN PATENT DOCUMENTS

| EP | 0586355 | 3/1994 |
|---|---|---|
| EP | 0 814 166 | 12/1997 |
| WO | WO 98/00533 | 1/1998 |
| WO | WO 02/06500 | 1/2002 |

OTHER PUBLICATIONS

Armstrong et al. Theor Appl Genet 84: 755-762, 1992.*
Armstrong et al. Maize Genetics Cooperation Newsletter 65: 92-93, 1991.*
Gardiner et al. Genetics 134: 917-930, 1993.*
Songstad et al. In vitro Cell Dev Biol-Plant 32:179-183, 1996.*
Armstrong and Green, "Establishment and maintenance of friable, embryogenic maize callus and the involvement of L-proline," *Planta*, 164:207-214, 1985.
Armstrong and Phillips, "Genetic and cytogenetic variation in plants regenerated from organogenic and friable, embryogenic tissue cultures of maize," *Crop Sci.*, 28:363-369, 1988.
Armstrong et al., "Development and availability of germplasm with high type II culture formation response," *Maize Gen. Coop. Newsletter*, 65:92-93, Mar. 1, 1991.
Armstrong et al., "Field evaluation of European corn borer control in progeny of 173 transgenic corn events expressing an insecticidal protein from *Bacillus thuringiensis*," *Crop Sci.*, 35:550-557, 1995.
Armstrong et al., "Improved tissue culture response of an elite maize inbred through backcross breeding, and identification of chromosomal regions important for regeneration by RFLP analysis," *Theor. Appl. Genet.*, 84:755-762, 1992.
Armstrong et al.; "Development and availability of germplasm with high type II culture formation response," *Maize Genetics Cooperation Newsletter*, 65:92-93, 1991.
Armstrong, Charles L.; "Regeneration of plants from somatic cell cultures: applications for in vitro genetic manipulation," In: The Maize Handbook, Springer-Verlag, New York, NY, pp. 663-671, 1994.
Beavis et al., "Identification of quantitative trait loci using a small sample of topcrossed and F4 progeny from maize," *Crop Sci.*, 34:882-896, 1994.
Ben Amer et al., "Chromosomal location of genes affecting tissue-culture response in wheat," *Plant Breeding*, 114:84-85, 1995.
Ben Amer et al., "Genetic mapping of QTL controlling tissue-culture response on chromosome 2B of wheat (*Triticum aestivum* L.) in relation to major genes and RFLP markers," *Theor. Appl. Genet.*, 94:1047-1052, 1997.
Bregitzer and Campbell, "Genetic markers associated with green and albino plant regeneration from embryogenic barley callus," *Crop Sci.*, 41:173-179, 2001.
Croon, et al.; "Request for extension of determination of nonregulated status to the additional regulated article: roundup ready corn line NK603," submitted to The Animal and Plant Health Inspection Service of the U.S. Department of Agriculture, Jan. 7, 2000.
Frame et al., "Production of transgenic maize from bombarded type II callus: effect of gold particle size and callus morphology on transformation efficiency," *In Vitro Cell Dev Biol*, 36:21-29, 2000.
Heck et al.; "Genomics, molecular genetics & biotechnology: development and characterization of a CP4 EPSPS-based, glyphosate-tolerant corn event," *Crop Sci.*, 44:329-339, 2005.
Kwon et al., "Marker-assisted selection for identification of plant regeneration ability of seed-derived calli in rice (*Oryza sativa* L.)," *Mol. Cells*, 12:103-106, 2001.

(Continued)

*Primary Examiner* — Shubo (Joe) Zhou
*Assistant Examiner* — Keith Robinson
(74) *Attorney, Agent, or Firm* — Dentons US LLP; Thomas P. McBride Esq.

(57) ABSTRACT

The current invention provides methods and compositions for producing an elite line of *Zea mays* enhanced for transformability. Compositions comprising an elite germplasm exhibiting increased transformability are disclosed. Further provided are methods for breeding maize such that enhanced transformability traits may be transferred to a desired germplasm. The plants and methods of the invention represent a valuable new tool for the creation of elite transgenic plants, preferably having one or more added beneficial characteristics.

6 Claims, 1 Drawing Sheet

(56) References Cited

OTHER PUBLICATIONS

Kwon et al., "Quantitative trait loci mapping associated with plant regeneration ability from seed derived calli in rice (*Oryza sativa* L.)," *Mol. Cells*, 11:64-67, 2001.

Lee et al., "Genetic analysis of totipotency in maize," 44th *Annual Maize Genetics Conference*, p. 64, Poster #54:54, 2002.

Lowe et al., "Marker assisted breeding for transformability in maize," *Mol. Breeding*, 18:229-239, 2006.

Mano et al., "Mapping genes for callus growth and shoot regeneration in barley (*Hordeum vulgare* L.," *Breeding Science*, 46:137-142, 1996.

Mohan et al., "Genome mapping, molecular markers and marker-assisted selection in crop plants," *Molecular Breeding*, 3:87-103, 1997.

Murigneux et al., "Genotypic variation of quantitative trait loci controlling in vitro androgenesis in maize," *Genome*, 37:970-976, 1994.

Notice: "Monsanto Co.; Extension of determination of nonregulated status for corn genetically engineered for glyphosate herbicide tolerance," *Federal Register*, 65(169):52693-52694, 2000.

O'Kennedy et al., "Stable transformation of Hi-II maize using the particle inflow gun," *South African Journal of Science*, 94:188-192, 1998.

Schiantarelli et al., "Use of recombinant inbread lines (RILs) to identify, locate and map major genes and quantitative trait loci involved with in vitro regeneration ability in *Arabidopsis thaliana*," *Theor. Appl. Genet.*, 102:335-341, 2001.

Songstad et al., "Production of transgenic maize plants and progeny by bombardment of Hi-II immature embryos," *In Vitro Cell. Dev. Biol.—Plant: Journal of the Tissue Culture Association*, 32:179-183, 1996.

Taguchi-Shiobara et al., "Mapping quantitative trait loci associated with regeneration ability of seed callus in rice, *Oryza sativa* L.," *Theor. Appl. Genet.*, 95:828-833, 1997.

Takeuchi et al., "RFLP mapping of QTLs influencing shoot regeneration from mature seed-derived calli in rice," *Crop Sci.*, 40:245-247, 2000.

Welsh et al., "Fingerprinting genomes using PCR with arbitrary primers," *Nucleic Acids Res.*, 18(24):7213-7218, 1990.

Zhang et al., "Variation in the inheritance of expression among subclones for unselected (uidA) and selected (bar) transgenes in maize (*Aea mays* L.)," *Theor Appl Genet*, 92:752-761, 1996.

Zhao et al., "High throughput genetic transformation mediated by *Agrobacterium tumefaciens* in maize," *Molecular Breeding*, 8:323-333, 2001.

Zhong et al., "Analysis of the functional activity of the 1.4-kb 5'-region of the rice actin 1 gene in stable transgenic plants of maize (*Zea mays* L.)," *Plant Science*, 116:73-84, 1996.

\* cited by examiner

| Male | Female | IE/Progeny | Observations |
|---|---|---|---|
| Hi-II | FBLL | F1 | |
| Hi-IIxFBLL (F1) | FBLL | BC1 | Isolate immature BC1 embryos |
| | | | Approximately 9% showed culturability |
| | | | Regenerated over 250 individual plants |
| | | | RFLP markers (Table 1) identified on chromosomes 1, 2, 3, 6, 10 |
| | | | Plants grown to maturity |
| Hi-IIxFBLL (BC1) | FBLL | BC2 | Five "A" ears selected for chromosomes 1, 3, 10 |
| FBLL | "A" or "B" | BC3 | Five "B" ears selected for chromosomes 1, 2, 6 |
| Hi-IIxFBLL (BC3) | Hi-IIxFBLL (BC3) | BC3F1 | RFLP & SSR markers (Table 2) identified on chromosomes 1, 3, 6, 10 |
| | | | self or sib pollinated |
| | | | Immature embryos isolated from 2 ears |
| | | | 5% of embryos produced regenerable callus |
| | | | Plants more similar in appearance to FBLL than Hi-II |
| Hi-IIxFBLL(BC3F1) | Hi-IIxFBLL(BC3F1) | BC3F2 | Self pollinated |
| | | | BC3F2 used in transformation testing (Table 3) |
| | | | SSR markers applied |
| Hi-IIxFBLL(BC3F2) | Hi-IIxFBLL(BC3F2) | BC3F3 | Self pollinated |
| | | | BC3F3 used in first round hybrid yield test trials |
| | | | BC3F3 used in transformation testing (Tables 4 and 5) |
| | | | SSR markers identified on chromosomes 1, 3, 6, 10 |
| | | | SSR markers indicated fixedness of lines |
| Hi-IIxFBLL(BC3F3) | Hi-IIxFBLL(BC3F3) | BC3F4 | Self pollinated or sib pollinated |
| | | | SSR markers indicated fixedness of lines (Table 6) |
| | | | BC3F4 used in transformation testing (Tables 7) |
| | | | SNP markers applied to determine fixedness (Table 9) |
| Hi-IIxFBLL(BC3F4) | Hi-IIxFBLL(BC3F4) | BC3F5 | Self pollinated |
| | | | BC3F5 used in transformation testing (Table 8) |
| | | | BC3F5 are useful for second round hybrid yield testing |
| | | | Two lead lines selected |
| Hi-IIxFBLL(BC3F5) | Hi-IIxFBLL(BC3F5) | BC3F6 | Are useful for self pollination |
| | | | Are useful for inbred yield trials | and # METHODS AND COMPOSITIONS FOR PRODUCTION OF MAIZE LINES WITH INCREASED TRANSFORMABILITY This application is a divisional of U.S. application Ser. No. 10/455,229, filed Jun. 5, 2003 now U.S. Pat. No. 7,759,545, the disclosure of which is incorporated herein by reference in its entirety, which application claims the priority of provisional patent application Ser. No. 60/386,522, filed Jun. 6, 2002, the entire disclosure of which is specifically incorporated herein by reference.

BACKGROUND OF THE INVENTION

1. Field of the Invention

The present invention is in the field of plant transformation, especially as it pertains to *Zea mays*. More specifically, the invention relates to methods and compositions for the production of plant varieties with improved transformability.

2. Description of the Related Art

In addition to breeding, the ability to culture and regenerate plants via tissue culture techniques has been useful in the study and advancement of plant manipulations. Beneficial alterations in the genome may occur during the culturing and regeneration of a plant such that new or improved agronomic traits result. Culturability of a given crop plant appears to vary with the germplasm used, with some lines being easier to culture and regenerate than others. In many instances, however, plants with superior agronomic traits tend to exhibit poor culturing and regeneration characteristics while plants that are more easily cultured and regenerated are often agronomically poor.

In corn, for example, agronomically desirable lines such as B73 or FBLL show reduced culturability and regenerability relative to agronomically poor, yet culturable lines such as A188 or H99. It is the experience of the present inventors that a genotype may be culturable but not transformable. For example, immature embryos were isolated from a number of elite corn lines and tested for culturability and transformability; while a number of lines formed callus, most of the lines were not transformable under the conditions employed.

Work by Armstrong and others (1991, 1992) showed that it was possible to interbreed a more culturable, agronomically poor maize line (A188) with an agronomically desirable, less transformable line (B73) to produce a novel line with increased culturability and regeneration (Hi-II). Marker analysis of the line was carried out and identified several chromosomal regions that appeared to confer increased culturability on the less culturable genetic background. More specifically, Armstrong and others (1992) identified markers on chromosomes 1, 2, 3, and 9 as being associated with enhanced culturability and regenerability. A marker on chromosome 9, c595, was reported to be particularly relevant for the formation of callus in the new germplasm as well as the ability to regenerate plants.

Breeding is a traditional and effective means of transferring the traits of one plant to another plant. Marker assisted breeding is a means of enhancing traditional breeding and allowing for selection of biochemical, yield or other less visible traits during the breeding process. Transformation is a new molecular technique that is effective in transferring DNA from a variety of sources into a plant in order to obtain plants with improved agronomic or novel traits. While breeding work has been carried out to improve plant culture and regeneration, virtually no research has been carried out to identify and breed for chromosomal regions that are linked with enhanced transformation characteristics.

Knowledge of the markers, chromosomal regions and genes that result in increased transformability would be beneficial to the art of plant transformation. Transformability of plants such as corn plants often varies with the germplasm, with some lines being more transformable than other lines. Typically, more transformable lines are typically agronomically poor (for example Hi-II) while lines with superior or desired agronomic traits are less transformable (for example FBLL). If a desired gene is introduced into an agronomically poor line, it is then commonly introgressed into an elite or superior line for testing such parameters as efficacy of the introduced gene as well as to test the effect of the gene on such traits as yield, kernel quality and plant phenotype. Thus, to enable meaningful performance testing in earlier generations, it would be advantageous to be able to introduce the genetic components resulting in enhanced transformability into agronomically superior lines.

The present invention overcomes this deficiency in the art by providing a method of breeding for increased transformability and resultant maize plants.

SUMMARY OF THE INVENTION

In one aspect, the present invention provides methods of breeding crop plants for increased transformability as well as plant compositions exhibiting increased transformability, particularly maize plants. In one embodiment, the invention provides a process for producing an agronomically elite and transformable corn plant, comprising the steps of producing a population of plants by introgressing a chromosomal locus mapping to chromosome bin 6.02 to 6.04 or bin 10.04 to 10.06 from a more transformable maize genotype into a less transformable maize genotype. In certain embodiments of the invention, the process for producing an agronomically elite and transformable corn plant also comprises introgressing at least one chromosomal locus mapping to chromosome bins 1.03 to 1.06, 1.08 to 1.11, or 3.05 to 3.07 from a transformable variety into an agronomically elite variety.

The transformable parent used in the breeding may be a hybrid plant, particularly of the Hi-II genotype. The agronomically elite parent used in the breeding may be an inbred line, for example, of the FBLL genotype, a sample of the seed of which were deposited as ATCC accession No. PTA-3713. The method of breeding for enhanced transformability disclosed herein may further comprise producing progeny of any generation of the transformable, agronomically elite corn variety.

The current invention also provides methods and composition relating to two lines of maize germplasm that exhibit enhanced transformability. "FBLL MAB" means a transformable elite corn variety developed by a method of the invention and prepared using inbred corn line FBLL, including corn variety 178-187-20 and 178-74-25. A sample of the seed from FBLL MAB variety 178-187-20 has been deposited under ATCC accession No. PTA-5183 and a sample of the seed from FBLL MAB variety 178-74-25 has been deposited under ATCC accession No. PTA-5182.

In one embodiment, the invention provides an essentially homogeneous population of the seed or plants of the corn variety 178-187-20 or 178-74-25 The invention further provides a transgenic corn plant produced by transforming the genome of a tissue produced from any generation of seed or plant of the variety 178-187-20 or 178-74-25, progeny of such transformed plants and seed produced by crossing any corn line with the transformed plant produced using the seed and methods provided in the invention.

BRIEF DESCRIPTION OF THE DRAWINGS

The following drawing forms part of the present specification and is included to further demonstrate certain aspects of the invention. The invention may be better understood by reference to the drawing in combination with the detailed description of specific embodiments presented herein:

FIG. 1 illustrates a breeding schematic indicating crosses performed to generate an elite inbred female line with enhanced transformability.

DETAILED DESCRIPTION OF THE INVENTION

One important aspect in the production of genetically engineered crop plants such as corn, is the ability to quickly and easily generate ample numbers of transformed plants. It would be useful to have crop lines that are highly transformable so as to reduce the amount of laboratory work required to generate a plant with a desired foreign DNA insert. It is especially useful if the crop lines demonstrating increased transformability are maize lines.

A plant line, such as a maize inbred or hybrid, is said to exhibit "enhanced transformability" if the transformation efficiency of the line is greater than a parental line under substantially identical conditions of transformation. Transformation efficiency is a measure of the number of transgenic plants regenerated relative to the number of units of starting material (for example, immature embryos, pieces of callus and the like) exposed to an exogenous DNA, regardless of the type of starting material, the method of transformation, or the means of selection and regeneration. Under the breeding and transformation conditions described herein, a line is considered to exhibit enhanced transformability if a line exposed to the breeding process has a higher transformation efficiency that the starting parental line. For example, under the transformation conditions described herein, no transformants were recovered using an elite inbred line FBLL (U.S. Pat. No. 6,362,403, the entire disclosure of which is specifically incorporated herein by reference); however, following breeding with a transformable Hi-II line and transformation selection of progeny, an FBLL line with a transformation efficiency of about 5.28% was recovered. Thus for lines that have no or essentially no measurable transformability, an increase to a measurable transformability, e.g., to at least 1% to 5% or higher, is an indication of enhanced transformability.

For lines that have a measurable transformability, e.g., 0.001% to 0.01% or more, enhanced transformability can be measured by a fold increase. Transformation efficiency of the progeny germplasm after breeding may be enhanced from about two-fold to about three-fold beyond the transformation efficiency of the parental line. Alternatively, the transformation efficiency of the progeny germplasm after breeding may be enhanced about three-fold to about five-fold beyond the transformation efficiency of the parental line. It is contemplated that transformation efficiencies of progeny lines after breeding may be increased about five-fold to about ten-fold, from about five-fold to twenty-fold, and from about five-fold to about fifty-fold, and even from about five-fold to about one hundred-fold beyond the transformation efficiency of the parental line. A line is considered to demonstrate enhanced transformability when, after marker assisted breeding and transformation testing as described in the instant invention, the line exhibits at least a three-fold increase in transformation efficiency over the parental line.

Another important aspect to consider in the production of genetically engineered crops such as maize, is the background or genetic makeup of the plant. It is often the case that plant varieties which demonstrate increased transformability are not agronomically desirable. Plants exhibiting desired agronomic traits are considered to be agronomically elite. For the purposes of this invention, an elite line has any desirable characteristics not found in the transformable line. Traits that may be considered to confer elitism include good seed set, good pollen set, excellent roots, good cold germination, good combining ability, tolerance to pests, tolerance to disease, tolerance to drought, tolerance to salts or metals, floral timing, timing between anthesis and silking, good lodging, upright leaves, good ear height, a good percentage of kernel moisture, high yield as an inbred, high yield as a hybrid, good plant height, stiff stalk and the like. Poehlman (1987) discloses a variety of characteristics and parameters that are considered desirable in agronomically elite lines.

In corn, for example, lines such as A188, H99 or Hi-II are easy to transform but are not high yielding and do not possess other desirable agronomic traits. It is preferred to test characteristics such as yield or grain quality in crop lines that are agronomically desirable. Thus, it would be useful in the art to be able to efficiently transform crop plants with desired agronomic traits as this would enable meaningful performance testing in earlier generations for parameters such as yield, grain quality or plant appearance. In addition, a reduction in the breeding time required before agronomic testing may result in reduced time to market for a finished product. It is especially useful if the lines with desired agronomic traits which also have increased transformability are maize lines.

The present invention overcomes limitations in the prior art of corn transformation by providing a method of breeding to enhance transformability. It is advantageous that maize lines exhibiting poor transformation capabilities can be bred according the methods disclosed herein to result in lines which show enhanced transformation. It is particularly advantageous that the method may be applied to elite lines to impart enhanced transformability in an agronomically desirable germplasm. The invention also identifies particular chromosomal bin locations important for the culturability, regeneration and transformation of lines showing enhanced transformation, particularly of germplasm resulting from the breeding of a poorly transformable elite inbred with a highly transformable line. The present invention also provides two elite inbred lines exhibiting enhanced transformation relative to the parental inbred line used for breeding the plants of the invention.

The method of the present invention was demonstrated using two maize lines, Hi-II and FBLL. One of skill in the art will recognize that any genotypes that are highly transformable yet exhibit undesirable agronomic characteristics may also be used including, but not limited to, H99 and A188. Hi-II germplasm demonstrates good transformability but has poor agronomic characteristics. In contrast, FBLL is an agronomically elite inbred line with desirable agronomic traits that exhibits poor transformability. Using FBLL typically as the recurrent female parent, several generations of marker-assisted breeding were carried out to generate novel FBLL-MAB elite lines. Progeny from various generations were tested for culturability, regenerability and transformability as well as selected for desirable agronomic traits. Lines exhibiting both desirable agronomic characteristics and enhanced transformability were selected and selfed for several generations. Marker analysis indicated that five regions associated with chromosomes 1, 3, 6 and 10 were associated with the enhanced transformability phenotype. Analysis also indicated that the lines exhibiting enhanced transformability also contained regions on chromosomes 4 and 8. Hybrids made with two FBLL MAB lines demonstrating increased transformability indicated that yield was not significantly affected relative to commercially desired levels.

Regions located on chromosome 10 and chromosome 6 were identified by the present inventors and were not disclosed by Armstrong et al. (1992). In addition, markers on chromosomes 2 and 9 previously disclosed by Armstrong et al. (1992) were not identified by the present inventors and thus, while these regions may be important for culturability or regenerability, may not contribute to transformability or enhanced transformability. Lee et al. (2002), report the use of recombinant inbred lines (Mo17 (poor culturability) by H99 (good culturability)) to study callus initiation of the hybrids. Genes suggested to be in involved in the callus response were located to chromosomes 3, 5, 8 and 9. Markers used by the present inventors did not identify regions on chromosomes 5 or 9 as being associated with enhanced transformability.

I. QTLs

Inbred lines are lines that have been self-pollinated over many generations and elite inbred lines are lines that have been self-pollinated over many generations and, at the same time, selected based upon certain desired agronomic traits or other desired characteristics. A cross between two different homozygous plants produces a uniform population of hybrid plants that are heterozygous for many gene loci.

One may introduce an enhanced transformability trait into potentially any desired maize genetic background, for example, in the production of inbred lines suitable for production of hybrids, any other inbred lines, maize lines with desirable agronomic characteristics, or any maize line possessing an increased transformability trait. Using conventional plant breeding techniques, one may breed for enhanced transformability and maintain the trait in an inbred by self or sib-pollination.

Marker assisted introgression involves the transfer of a chromosome region defined by one or more markers from one germplasm to a second germplasm. An initial step in that process is the localization of the trait by gene mapping which is the process of determining the position of a gene relative to other genes and genetic markers through linkage analysis. The basic principle for linkage mapping is that the closer together two genes are on the chromosome, the more likely they are to be inherited together. Briefly, a cross is made between two genetically compatible but divergent parents relative to traits under study. Genetic markers are then used to follow the segregation of traits under study in the progeny from the cross (often a backcross (BC1), $F_2$, or recombinant inbred population).

Although a number of important agronomic characters are controlled by a single region on a chromosome (also known as a locus) or a single gene having a major effect on a phenotype, many economically important traits, such as yield and some forms of disease resistance, are quantitative in nature and involve many genes or loci. The term quantitative trait loci, or QTL, is used to describe regions of a genome showing qualitative or additive effects upon a phenotype. As used herein, QTL refers to a chromosomal region defined by particular, heritable genetic markers.

The current invention relates to the introgression in maize of genetic material, e.g, a QTL, which is capable of causing a plant to be more easily transformed. Quantitative trait loci have been found to be associated with a wide variety of traits in many types of plants. QTLs from monocots such as wheat, rice and maize, as well as from dicots such as *Arabidopsis, Brassica* and barley have been identified for traits such as, but not limited to, nitrogen-use efficiency drought tolerance, submergence tolerance, heterosis, quality traits in seeds, kernels and yield, insect, pest and disease resistance, pigmentation, root thickness and penetration ability, floral development, plant height and floral timing, tassel traits, fruit size, and other agronomic traits.

QTLs related to plant tissue culture and regeneration have been identified in wheat (Ben Amer et al., 1995; Ben Amer et al., 1997), rice (Taguchi-Shiobara et al., 1997; Takeuchi et. al., 2000; Kwon et al., 2001a, 2001b), *Arabidopsis* (Schiantarelli et al., 2001), barley (Mano et al., 1996; Bregitzer and Campbell, 2001) and corn (Armstrong et al., 1992; Murigneux et al., 1994). In one study in the dicot *Arabidopsis*, no correlation was found between the percentage of callus formed and the ability to regenerate plants (Schiantarelli et al., 2001). In general, it is believed that many QTLs or chromosomal regions contribute to the process of plant culturability, the ability to form somatic embryos and the ability to regenerate into fertile plants. Furthermore, different QTLs are believed to be involved in the various steps of plant tissue culture and plant regeneration. It is of further desirable interest to identify QTLs that contribute to enhanced transformability of a plant and thereby to be able to manipulate plant performance of crops, such as but not limited to, corn, wheat, rice and barley.

Culturability, embryogenesis and the ability to regenerate crop plants are useful in the pursuit of somaclonal variants and the production of beneficial phenotypic alterations of plants. Recovery of altered phenotypes in plants regenerated from callus varies depending upon the choice of crop line, and the conditions and duration of culturing. In some experiments in maize, somaclonal variation was observed in less than 4% of plants regenerated post-culture (Armstrong and Green, 1985) whereas in other experiments, regenerated plants exhibiting altered phenotypes or chimerism could be recovered at a rate of about 9% to about 50% (Armstrong and Phillips, 1988). In more directed experiments, maize plants exhibiting resistance to the herbicide imidazolinone were generated by mutations introduced into the acetohydroxyacid synthase gene during tissue culture and regeneration of A188×B73 plants in the presence of imidazolinone herbicide (U.S. Pat. Nos. 4,761,373; 5,304,732; 5,331,107; 5,718,079; each of which is incorporated herein by reference). Hibberd et al. (U.S. Pat. Nos. 4,581,847 and 4,642,411; both of which are incorporated herein by reference) report the use of plant cell culture to isolate and develop maize cell lines which over produce tryptophan in callus, plants and seeds. Thus, the ability to improve the culturability and regenerability of crop plants is beneficial as a tool for producing mutations leading to desired phenotypes and agronomic traits.

Early work by Armstrong et al. investigated the use of breeding (1991) and marker analysis (1992) to generate maize lines that were considered to be more culturable and regenerable than the parental maize lines. The parental lines utilized were a difficult to culture, agronomically desirable line (B73) and a highly culturable, agronomically poor line which had been shown to produce callus and regenerate plants (A188). Through a series of backcrosses and self-crosses, a more highly culturable line, named the "Hi-II" germplasm line, was developed. In comparison to the parental B73 line, the Hi-II line was found to be relatively easy to culture and from which healthy plants could be regenerated. RFLP analysis of markers which appeared to be associated with the increased culturability were located to chromosomes 1, 2, 3 and 9. The use of markers suggested that chromosomal regions of A188 remained in the B73 background, presumably allowing for the increased culturability and regenerability of the progeny Hi-II line. Of particular interest in this work was the marker c595 located on chromosome 9; it was suggested that a major gene or genes linked with marker c595 promote callus formation and plant regeneration. The Hi-II line was easily cultured and regenerated, but did not incorporate the agronomically desirable characteristics of B73.

It was desired to develop novel elite inbreds having enhanced transformability as well as the superior agronomic characteristics imparted by an elite inbred, in particular the inbred line FBLL. FBLL is an elite inbred line that is characterized by several agronomically desirable traits including good seed set, upright leaves, excellent roots, good cold germination and is a member of the stiff stalk heterotic group (U.S. Pat. No. 6,362,403, incorporated herein by reference in its entirety). Under the conditions used by the inventors, it was difficult to initiate sustainable cultures and produce transformants from the genotype FBLL. Furthermore, the Hi-II line was readily transformed with foreign DNA (Armstrong et al., 1995; Songstad, 1996; EP 0 586 355 A2). The present inventors identified chromosomal regions responsible for enhanced transformability in Hi-II and used marker assisted breeding to introgress these specific linkage blocks into an elite inbred germplasm, preferably FBLL.

Following crosses of Hi-II to FBLL, plants were selected based on the presence of QTLs from the elite parent and having the enhanced transformability and culturability of the Hi-II parent. The genome of the resultant inbred, and likewise hybrid combination, comprised substantially all the elite background and the chromosomal regions contributing to enhanced transformability.

It will be understood to those of skill in the art that other probes which more closely map the chromosomal regions as identified herein could be employed to identify crossover events. The chromosomal regions of the present invention facilitate introgression of increased transformability from readily transformable germplasm, such as Hi-II, into other germplasm, preferably elite inbreds. Larger linkage blocks likewise could be transferred within the scope of this invention as long as the chromosomal region enhances the transformability of a desirable inbred. Accordingly, it is emphasized that the present invention may be practiced using any molecular markers which genetically map in similar regions, provided that the markers are polymorphic between the parents.

II. Markers and Genetic Mapping of Additive Traits

A plant genetic complement can be defined by a genetic marker profile that can be considered a "fingerprint" of a genetic complement. For purposes of this invention, markers are preferably distributed evenly throughout the genome to increase the likelihood they will be near a quantitative trait locus or loci (QTL) of interest.

A. Gene Mapping Through Linkage

A sample first plant population may be genotyped for an inherited genetic marker to form a genotypic database. As used herein, an "inherited genetic marker" is an allele at a single locus. A locus is a position on a chromosome, and allele refers to conditions of genes; that is, different nucleotide sequences, at those loci. The marker allelic composition of each locus can be either homozygous or heterozygous.

Formation of a phenotypic database by quantitatively assessing one or more numerically representable phenotypic traits can be accomplished by making direct observations of such traits on progeny derived from artificial or natural self-pollination of a sample plant or by quantitatively assessing the combining ability of a sample plant.

By way of example, a plant line is crossed to, or by, one or more testers. Testers can be inbred lines, single, double, or multiple cross hybrids, or any other assemblage of plants produced or maintained by controlled or free mating, or any combination thereof For some self-pollinating plants, direct evaluation without progeny testing is preferred.

The marker genotypes are determined in the testcross generation and the marker loci are mapped To map a particular trait by the linkage approach, it is necessary to establish a positive correlation in inheritance of a specific chromosomal region with the inheritance of the trait. This may be relatively straightforward for simply inherited traits. In the case of more complex inheritance, such as with as quantitative traits, linkage will be much more difficult to discern. In this case, statistical procedures must be used to establish the correlation between phenotype and genotype. This will further necessitate examination of many offspring from a particular cross, as individual loci may have small contributions to an overall phenotype.

Coinheritance, or genetic linkage, of a particular trait and a marker suggests that they are physically close together on the chromosome. Linkage is determined by analyzing the pattern of inheritance of a gene and a marker in a cross. In order for information to be gained from a genetic marker in a cross, the marker must be polymorphic; that is, it must exist in different forms so that the chromosome carrying the mutant gene can be distinguished from the chromosome with the normal gene by the form of the marker it also carries. The unit of recombination is the centimorgan (cM). Two markers are one centimorgan apart if they recombine in meiosis once in every 100 opportunities that they have to do so. The centimorgan is a genetic measure, not a physical one, but a useful rule of thumb is that 1 cM is equivalent to approximately $10^6$ bp.

During meiosis, pairs of homologous chromosomes come together and exchange segments in a process called recombination. The farther an RFLP, or other genetic marker, is from a gene, the more chance there is that there will be recombination between the gene and the marker. In a linkage analysis, the coinheritance of marker and gene or trait are followed in a particular cross. The probability that their observed inheritance pattern could occur by chance alone, i.e., that they are completely unlinked, is calculated. The calculation is then repeated assuming a particular degree of linkage, and the ratio of the two probabilities (no linkage versus a specified degree of linkage) is determined. This ratio expresses the odds for (and against) that degree of linkage, and because the logarithm of the ratio is used, it is known as the logarithm of the odds, e.g. an lod score. A lod score equal to or greater than 3, for example, is taken to confirm that gene and marker are linked. This represents 1000:1 odds that the two loci are linked. Calculations of linkage is greatly facilitated by use of statistical analysis employing programs.

The genetic linkage of marker molecules can be established by a gene mapping model such as, without limitation, the flanking marker model reported by Lander and Botstein (1989), and the interval mapping, based on maximum likelihood methods described by Lander and Botstein (1989), and implemented in the software package MAPMAKER/QTL (Lincoln and Lander, 1990). Additional software includes Qgene, Version 2.23 (1996), Department of Plant Breeding and Biometry, 266 Emerson Hall, Cornell University, Ithaca, N.Y.). Use of Qgene software is a particularly preferred approach.

A maximum likelihood estimate (MLE) for the presence of a marker is calculated, together with an MLE assuming no QTL effect, to avoid false positives. A $\log_{10}$ of an odds ratio (LOD) is then calculated as: $LOD=\log_{10}$ (MLE for the presence of a QTL/MLE given no linked QTL).

The LOD score essentially indicates how much more likely the data are to have arisen assuming the presence of a QTL than in its absence. The LOD threshold value for avoiding a false positive with a given confidence, say 95%, depends on the number of markers and the length of the genome. Graphs indicating LOD thresholds are set forth in Lander and Botstein (1989), and further described by Arils and Moreno-González, 1993).

Additional models can be used. Many modifications and alternative approaches to interval mapping have been reported, including the use non-parametric methods (Kruglyak and Lander, 1995). Multiple regression methods or models can be also be used, in which the trait is regressed on a large number of markers (Jansen, 1994; Weber and Wricke, 1994). Procedures combining interval mapping with regression analysis, whereby the phenotype is regressed onto a single putative QTL at a given marker interval, and at the same time onto a number of markers that serve as 'cofactors,' have been reported by Jansen and Stam, (1994) and Zeng, (1994). Generally, the use of cofactors reduces the bias and sampling error of the estimated QTL positions (Utz and Melchinger, 1994), thereby improving the precision and efficiency of QTL mapping (Zeng, 1994). These models can be extended to multi-environment experiments to analyze genotype-environment interactions (Jansen et al., 1995).

B. Inherited Markers

A number of different markers are available for use in genetic mapping. These include RLFP restriction fragment length polymorphisms (RFLPs), isozymes, simple sequence repeats (SSRs or microsatellites) and single nucleotide polymorphisms (SNPs) These markers are known to those of skill in the arts of plant breeding and molecular biology.

Several genetic linkage maps have been constructed which have located hundreds of RFLP markers on all 10 maize chromosomes. Molecular maps based upon RFLP markers have been reported for maize by several researchers examining a wide variety of traits (Burr et al., 1988; Weber and Helentjaris, 1989; Stuber et al., 1992; Coe, 1992; Gardiner et al., 1993; Sourdille et al., 1996). One of skill in the art will recognize that genetic markers in maize are well known to those of skill in the art and are updated on a regular basis (www.agron.missouri.edu).

Another, type of genetic marker includes amplified simple sequence length polymorphisms (SSLPs) (Williams et al., 1990) more commonly known as simple sequence repeats (SSRs) or microsatellites (Taramino and Tingey, 1996; Senior and Heun, 1993). SSRs are regions of the genome which are characterized by numerous dinucleotide or trinucleotide repeats, e.g., AGAGAGAG. As with RFLP maps, genetic linkage maps have been constructed which have located hundreds of SSR markers on all 10 maize chromosomes.

Genetic linkage maps constructed using publicly available SNP markers are still in their infancy. For example, 21 loci along chromosome 1 have been mapped using SNPs (Tenaillon et al., 2001) and over 300 polymorphic SNP markers have been identified from approximately 700 expressed sequence tags or genes from a comparison of MO17 and B73 (Bhattramakki et al., 2000).

One of skill in the art would recognize that many types of molecular markers are useful as tools to monitor genetic inheritance and are not limited to isozymes, RFLPs, SSRs and SNPs, and one of skill would also understand that a variety of detection methods may be employed to track the various molecular markers. One skilled in the art would also recognize that markers of different types may be used for mapping, especially as technology evolves and new types of markers and means for identification are identified.

C. Scoring of Markers

For purposes of this invention, inherited marker genotypes maybe converted to numerical scores, e.g., if there are 2 forms of an RFLP, or other marker, designated A and B, at a particular locus using a particular enzyme, then diploid complements converted to a numerical score, for example, are AA=2, AB=1, and BB=0; or AA=1, AB=0 and BB=1. The absolute values of the scores are not important. What is important is the additive nature of the numeric designations. The above scores relate to codominant markers. A similar scoring system can be given that is consistent with dominant markers.

III. Marker Assisted Breeding

The present invention provides a *Zea mays* plant with increased transformability selected for by use of marker assisted breeding wherein a population of plants are selected for an enhanced transformability trait. The selection comprises probing genomic DNA for the presence of marker molecules that are genetically linked to an allele of a QTL associated with enhanced transformability in the maize plant, where the alleles of a quantitative trait locus are also located on linkage groups on chromosomes 1, 3, 6 or 10 of a corn plant. The molecular marker is a DNA molecule that functions as a probe or primer to a target DNA molecule of a plant genome.

An $F_2$ population is the first generation of selfing after the hybrid seed is produced. Recombinant inbred lines (RIL) (genetically related lines; usually $>F_5$, developed from continuously selfing $F_2$ lines towards homozygosity) can be used as a mapping population. Information obtained from dominant markers can be maximized by using RIL because all loci are homozygous or nearly so.

Backcross populations (e.g., generated from a cross between a desirable variety (recurrent parent) and another variety (donor parent) carrying a trait not present in the former) can also be utilized as a mapping population. A series of backcrosses to the recurrent parent can be made to recover most of its desirable traits. Thus a population is created consisting of individuals similar to the recurrent parent but each individual carries varying amounts of genomic regions from the donor parent. Backcross populations can be useful for mapping dominant markers if all loci in the recurrent parent are homozygous and the donor and recurrent parent have contrasting polymorphic marker alleles (Reiter et al., 1992).

Another useful population for mapping are a near-isogenic lines (NIL). NILs are created by many backcrosses to produce an array of individuals that are nearly identical in genetic composition except for the desired trait or genomic region can be used as a mapping population. In mapping with NILs, only a portion of the polymorphic loci are expected to map to a selected region. Mapping may also be carried out on transformed plant lines.

IV. Methods for Genetic Analysis of Plants with Enhanced Transformability

Many methods may be used for detecting the presence or absence of the enhanced transformability QTLs of the current invention. Particularly, genetic markers which are genetically linked to the QTLs defined herein will find use with the current invention. Such markers may find particular benefit in the breeding of maize plants with increased transformability.

This will generally comprise using genetic markers tightly linked to the QTLs defined herein to determine the genotype of the plant of interest at the relevant loci. Examples of particularly advantageous genetic markers for use with the current invention, will be RFLPs and PCR based markers such as those based on micro satellite regions (SSRs) or single nucleotide polymorphisms (SNPs).

A number of standard molecular biology techniques are useful in the practice of the invention. The tools are useful not only for the evaluation of markers, but for the general molecular and biochemical analyses of a plant for a given trait of interest. Such molecular methods include, but are not limited to, template dependent amplification methods such as PCR or reverse transcriptase PCR, protein analysis for monitoring expression of exogenous DNAs in a transgenic plant, including Western blotting and various protein gel detection methods, methods to examine DNA characteristics including Southern blotting, means for monitoring gene expression such as Northern blotting, and other methods such as gel chromatography, high performance liquid chromatography and the like.

V. Breeding of Maize with Enhanced Transformability in Accordance with the Invention Breeding techniques take advantage of a plant's method of pollination. There are two general methods of pollination: self-pollination which occurs if pollen from one flower is transferred to the same or another flower of the same plant, and cross-pollination which occurs if pollen comes to it from a flower on a different plant. Plants that have been self-pollinated and selected for type over many generations become homozygous at almost all gene loci and produce a uniform population of true breeding progeny, homozygous plants.

In development of suitable inbreds, pedigree breeding may be used. The pedigree breeding method for specific traits involves crossing two genotypes. Each genotype can have one or more desirable characteristics lacking in the other; or, each genotype can complement the other. If the two original parental genotypes do not provide all of the desired characteristics, other genotypes can be included in the breeding population. Superior plants that are the products of these crosses are selfed and are again advanced in each successive generation. Each succeeding generation becomes more homogeneous as a result of self-pollination and selection. Typically, this method of breeding involves five or more generations of selfing and selection: $S_1 \rightarrow S_2$; $S_2 \rightarrow S_3$; $S_3 \rightarrow S_4$; $S_4 \rightarrow S_5$, etc. A selfed generation (S) may be considered to be a type of filial generation (F) and may be named F as such. After at least five generations, the inbred plant is considered genetically pure.

Breeding may also encompass the use of double haploid, or dihaploid, crop lines.

A. Backcrossing

Backcrossing transfers specific desirable traits, such as the increased transformability QTL loci of the current invention, from one inbred or non-inbred source to an inbred that lacks that trait. This can be accomplished, for example, by first crossing a superior inbred (A) (recurrent parent) to a donor inbred (non-recurrent parent), which carries the appropriate gene(s) for the trait in question (Fehr, 1987). The progeny of this cross are then mated back to the superior recurrent parent (A) followed by selection in the resultant progeny for the desired trait to be transferred from the non-recurrent parent. Such selection can be based on genetic assays, as mentioned below, or alternatively, can be based on the phenotype of the progeny plant. After five or more backcross generations with selection for the desired trait, the progeny are heterozygous for loci controlling the characteristic being transferred, but are like the superior parent for most or almost all other genes. The last generation of the backcross is selfed, or sibbed, to give pure breeding progeny for the gene(s) being transferred, in the case of the instant invention, loci providing the plant with enhanced transformability.

In one embodiment of the invention, the process of backcross conversion may be defined as a process including the steps of:

(a) crossing a plant of a first genotype containing one or more desired gene, DNA sequence or element, such as the QTLs of the present invention, to a plant of a second genotype lacking said desired gene, DNA sequence or element;

(b) selecting one or more progeny plant containing the desired gene, DNA sequence or element;

(c) crossing the progeny plant to a plant of the second genotype; and (d) repeating steps (b) and (c) for the purpose of transferring said desired gene, DNA sequence or element from a plant of a first genotype to a plant of a second genotype.

Introgression of a particular DNA element or set of elements into a plant genotype is defined as the result of the process of backcross conversion. A plant genotype into which a DNA sequence has been introgressed may be referred to as a backcross converted genotype, line, inbred, or hybrid. Similarly a plant genotype lacking said desired DNA sequence may be referred to as an unconverted genotype, line, inbred, or hybrid. During breeding, the genetic markers linked to enhanced transformability may be used to assist in breeding for the purpose of producing maize plants with increased transformability.

It is to be understood that the current invention includes conversions comprising one, two, three or all of the QTLs of the present invention. Therefore, when the term enhanced transformability or increased transformability converted plant is used in the context of the present invention, this includes any gene conversions of that plant. Backcrossing methods can therefore be used with the present invention to introduce the enhanced transformability trait of the current invention into any inbred by conversion of that inbred with one, two three, or all of the enhanced transformability loci, with all loci being preferred.

The selection of a suitable recurrent parent is an important step for a successful backcrossing procedure. The goal of a backcross protocol is to alter or substitute a trait or characteristic in the original inbred. To accomplish this, one or more loci of the recurrent inbred is modified or substituted with the desired gene from the nonrecurrent parent, while retaining essentially all of the rest of the desired genetic, and therefore the desired physiological and morphological, constitution of the original inbred. The choice of the particular nonrecurrent parent will depend on the purpose of the backcross, which in the case of the present invention will be to add the increased transformability trait to improve agronomically important varieties. The exact backcrossing protocol will depend on the characteristic or trait being altered to determine an appropriate testing protocol. Although backcrossing methods are simplified when the characteristic being transferred is a dominant allele, a recessive allele may also be transferred. In this instance it may be necessary to introduce a test of the progeny to determine if the desired characteristic has been successfully transferred. In the case of the present invention, one may test the transformability of progeny lines generated during the backcrossing program as well as using marker assisted breeding to select lines based upon markers rather than visual traits.

Backcrossing may additionally be used to convert one or more single gene traits into an inbred or hybrid line having the enhanced transformability of the current invention. Many single gene traits have been identified that are not regularly selected for in the development of a new inbred but that can be improved by backcrossing techniques. Single gene traits may or may not be transgenic, examples of these traits include but are not limited to, male sterility, waxy starch, herbicide resistance, resistance for bacterial, fungal, or viral disease, insect resistance, male fertility, enhanced nutritional quality, industrial usage, yield stability and yield enhancement. These genes are generally inherited through the nucleus. Some known exceptions to this are the genes for male sterility, some of which are inherited cytoplasmically, but still act as single gene traits.

Direct selection may be applied where the single gene acts as a dominant trait. An example might be the herbicide resistance trait. For this selection process, the progeny of the initial cross are sprayed with the herbicide prior to the backcrossing. The spraying eliminates any plants which do not have the desired herbicide resistance characteristic, and only those plants which have the herbicide resistance gene are used in the subsequent backcross. This process is then repeated for all additional backcross generations.

The waxy characteristic is an example of a recessive trait. In this example, the progeny resulting from the first backcross generation (BC1) must be grown and selfed. A test is then run on the selfed seed from the BC1 plant to determine which BC1 plants carried the recessive gene for the waxy trait. In other recessive traits, additional progeny testing, for example growing additional generations such as the BC1S1 may be required to determine which plants carry the recessive gene.

B. Hybrid Production

The development of uniform corn plant hybrids requires the development of homozygous inbred plants, the crossing of these inbred plants, and the evaluation of the crosses. Pedigree breeding and recurrent selection are examples of breeding methods used to develop inbred plants from breeding populations. Those breeding methods combine the genetic backgrounds from two or more inbred plants or various other broad-based sources into breeding pools from which new inbred plants are developed by selfing and selection of desired phenotypes. The new inbreds are crossed with other inbred plants and the hybrids from these crosses are evaluated to determine which of those have commercial potential.

A single cross hybrid corn variety is the cross of two inbred plants, each of which has a genotype which complements the genotype of the other. The hybrid progeny of the first generation is designated $F_1$. Preferred $F_1$ hybrids are more vigorous than their inbred parents. This hybrid vigor, or heterosis, is manifested in many polygenic traits, including markedly improved higher yields, better stalks, better roots, better uniformity and better insect and disease resistance. In the development of hybrids only the $F_1$ hybrid plants are sought. An $F_1$ single cross hybrid is produced when two inbred plants are crossed. A double cross hybrid is produced from four inbred plants crossed in pairs (A×B and C×D) and then the two $F_1$ hybrids are crossed again (A×B)×(C×D).

As a final step, maize breeding generally combines two inbreds to produce a hybrid having a desired mix of traits. Getting the correct mix of traits from two inbreds in a hybrid can be difficult, especially when traits are not directly associated with phenotypic characteristics. In a conventional breeding program, pedigree breeding and recurrent selection breeding methods are employed to develop new inbred lines with desired traits. Maize breeding programs attempt to develop these inbred lines by self-pollinating plants and selecting the desirable plants from the populations. Inbreds tend to have poorer vigor and lower yield than hybrids; however, the progeny of an inbred cross usually evidences vigor. The progeny of a cross between two inbreds is often identified as an $F_1$ hybrid. In traditional breeding $F_1$ hybrids are evaluated to determine whether they show agronomically important and desirable traits. Identification of desirable agronomic traits has typically been done by breeders' expertise. A plant breeder identifies a desired trait for the area in which his plants are to be grown and selects inbreds which appear to pass the desirable trait or traits on to the hybrid.

In the production of a commercially viable hybrid, one may wish to produce many different hybrids and progressively eliminate various lines based on detailed evaluations of their phenotype, including formal comparisons with commercially successful hybrids. Strip trials are one such means to compare the phenotypes of hybrids grown in as many environments as possible. Strip trials are preferably performed in many environments to assess overall performance of new hybrids and to select optimum growing conditions. Because the corn is grown in close proximity, environmental factors that affect gene expression, such as moisture, temperature, sunlight and pests, are minimized. For a decision to be made that a hybrid is worth making commercially available, it is not necessary that the hybrid be better than all other hybrids. Rather, significant improvements must be shown in at least some traits that would create improvements in some niches.

Hybrid plants having the increased transformability of the current invention may be made by crossing a plant having increased transformability to a second plant lacking the enhanced transformability. "Crossing" a plant to provide a hybrid plant line having an increased transformability relative to a starting plant line, as disclosed herein, is defined as the techniques that result in the introduction of increased transformability into a hybrid line by crossing a starting inbred with a second inbred plant line that comprises the increased transformability trait. To achieve this one would, generally, perform the following steps:

(a) plant seeds of the first inbred and a second inbred (donor plant line that comprises the enhanced transformability trait as defined herein;
(b) grow the seeds of the first and second parent plants into plants that bear flowers;
(c) allow cross pollination to occur between the plants; and
(d) harvest seeds produced on the parent plant bearing the female flower.

VI. Methods for Plant Transformation

Methods and compositions for transforming plants by introducing an exogenous DNA into a plant genome in the practice of this invention can include any of the well-known and demonstrated methods. Preferred methods of plant transformation are microprojectile bombardment as illustrated in U.S. Pat. Nos. 5,015,580; 5,550,318; 5,538,880; 6,160,208; 6,399,861 and 6,403,865 and *Agrobacterium*-mediated transformation as illustrated in U.S. Pat. Nos. 5,635,055; 5,824,877; 5,591,616; 5,981,840 and 6,384,301, all of which are incorporated herein by reference.

Transformation methods useful in the practice of this invention are preferably practiced in tissue culture on media and in a controlled environment. "Media" refers to the numerous liquid, solid, or semi-solid nutrient mixtures that are used to grow cells in vitro, that is, outside of the intact living organism. Recipient cell targets include, but are not limited to, meristem cells, callus, immature embryos and gametic cells such as microspores, pollen, sperm and egg cells.

"Propagation" or "propagating" as used herein means the process of multiplying or breeding plant material. Therefore, propagation may involve maintaining a viable tissue on a media, e.g. a callus tissue on a solid medium, or growing a plant from seed or tissue, such as callus and cuttings.

As used herein "regeneration" means the process of growing a plant from a plant cell (e.g., plant protoplast, callus or explant). It is contemplated that any cell from which a fertile plant may be regenerated is useful as a recipient cell. Callus may be initiated from tissue sources including, but not limited to, immature embryos, seedling apical meristems, microspores and the like. Those cells which are capable of proliferating as callus also are recipient cells for genetic transformation. Practical transformation methods and materials for making transgenic plants of this invention, e.g. various media and recipient target cells, transformation of immature embryos and subsequent regeneration of fertile transgenic plants are disclosed in U.S. Pat. No. 6,194,636 and U.S. patent application Ser. No. 09/757,089, both of which are incorporated herein by reference.

As used herein a "transgenic" organism is one whose genome has been altered by the incorporation of foreign genetic material or additional copies of native genetic material, e.g. by transformation or recombination. The transgenic organism may be a plant, mammal, fungus, bacterium or virus. As used herein "transgenic plant" means a plant or progeny plant of any subsequent generation derived therefrom, wherein the DNA of the plant or progeny thereof contains an introduced exogenous DNA not originally present in a non-transgenic plant of the same strain. The transgenic plant may additionally contain sequences which are native to the plant being transformed, but wherein the exogenous DNA has been altered in order to alter the level or pattern of expression of the gene.

As used herein an "$R_o$ transgenic plant" is a plant which has been directly transformed with an exogenous DNA or has been regenerated from a cell or cell cluster which has been transformed with an exogenous DNA. As used herein "progeny" means any subsequent generation, including the seeds and plants therefrom, which is derived from a particular parental plant or set of parental plants; the resultant progeny line may be inbred or hybrid. Progeny of a transgenic plant of this invention can be, for example, self-crossed, crossed to a transgenic plant, crossed to a non-transgenic plant, and/or back crossed.

VII. Production and Characterization of Stably Transformed Plants

The present invention contemplates the use of polynucleotides which encode a protein or RNA product effective for imparting a desired characteristic to a plant, for example, increased yield. Such polynucleotides are assembled in recombinant DNA constructs using methods known to those of ordinary skill in the art. A useful technology for building DNA constructs and vectors for transformation is the GATEWAY™ cloning technology (available from Invitrogen Life Technologies, Carlsbad, Calif.) which uses the site-specific recombinase LR cloning reaction of the Integrase/att system from bacteriophage lambda vector construction, instead of restriction endonucleases and ligases. The LR cloning reaction is disclosed in U.S. Pat. Nos. 5,888,732 and 6,277,608, U.S. Patent Application Publications 2001283529, 2001282319 and 20020007051, all of which are incorporated herein by reference. The GATEWAY™ Cloning Technology Instruction Manual which is also supplied by Invitrogen also provides concise directions for routine cloning of any desired RNA into a vector comprising operable plant expression elements.

As used herein, "exogenous DNA" refers to DNA which does not naturally originate from the particular construct, cell or organism in which that DNA is found. Recombinant DNA constructs used for transforming plant cells will comprise exogenous DNA and usually other elements as discussed below. As used herein "transgene" means an exogenous DNA which has been incorporated into a host genome or is capable of autonomous replication in a host cell and is capable of causing the expression of one or more cellular products. Exemplary transgenes will provide the host cell, or plants regenerated therefrom, with a novel phenotype relative to the corresponding non-transformed cell or plant. Transgenes may be directly introduced into a plant by genetic transformation, or may be inherited from a plant of any previous generation which was transformed with the exogenous DNA.

As used herein "gene" or "coding sequence" means a DNA sequence from which an RNA molecule is transcribed. The RNA may be an mRNA which encodes a protein product, an RNA which functions as an anti-sense molecule, or a structural RNA molecule such as a tRNA, rRNA, or snRNA, or other RNA. As used herein "expression" refers to the combination of intracellular processes, including transcription and translation, undergone by a DNA molecule, such as a structural gene to produce a polypeptide, or a non-structural gene to produce an RNA molecule.

As used herein "promoter" means a region of DNA sequence that is essential for the initiation of transcription of RNA from DNA; this region may also be referred to as a "5' regulatory region." Promoters are located upstream of DNA to be translated and have regions that act as binding sites for RNA polymerase and have regions that work with other factors to promote RNA transcription. More specifically, basal promoters in plants comprise canonical regions associated with the initiation of transcription, such as CAAT and TATA boxes. The TATA box element is usually located approximately 20 to 35 nucleotides upstream of the site of initiation of transcription. The CAAT box element is usually located approximately 40 to 200 nucleotides upstream of the start site of transcription. The location of these basal promoter elements result in the synthesis of an RNA transcript comprising some number of nucleotides upstream of the translational ATG start site. The region of RNA upstream of the ATG is commonly referred to as a 5' untranslated region or 5' UTR. It is possible to use standard molecular biology techniques to make combinations of basal promoters, that is regions comprising sequences from the CAAT box to the translational start site, with other upstream promoter elements to enhance or otherwise alter promoter activity or specificity.

As is well known in the art, recombinant DNA constructs typically also comprise other regulatory elements in addition to a promoter, such as but not limited to 3' untranslated regions (such as polyadenylation sites), transit or signal peptides and marker genes elements. For instance, see U.S. Pat. No. 6,437,217 which discloses a maize RS81 promoter, U.S. Pat. No. 5,641,876 which discloses a rice actin promoter, U.S. Pat. No. 6,426,446 which discloses a maize RS324 promoter, U.S. Pat. No. 6,429,362 which discloses a maize PR-1 promoter, U.S. Pat. No. 6,232,526 which discloses a maize A3 promoter, U.S. Pat. No. 6,177,611 which discloses constitutive maize promoters, U.S. Pat. No. 6,433,252 which discloses a maize L3 oleosin promoter, U.S. Pat. No. 6,429,357 which discloses a rice actin 2 promoter and intron, U.S. Pat. No. 5,837,848 which discloses a root specific promoter, U.S. Pat. No. 6,084,089 which discloses cold inducible promoters, U.S. Pat. No. 6,294,714 which discloses light inducible promoters, U.S. Pat. No. 6,140,078 which discloses salt inducible promoters, U.S. Pat. No. 6,252,138 which discloses pathogen inducible promoters, U.S. Pat. No. 6,175,060 which discloses phosphorus deficiency inducible promoters, U.S. Patent Application Publication 2002/0192813A1 which discloses 5′, 3′ and intron elements useful in the design of effective plant expression vectors, U.S. patent application Ser. No. 09/078,972 which discloses a coixin promoter, and U.S. patent application Ser. No. 09/757,089 which discloses a maize chloroplast aldolase promoter, all of which are incorporated herein by reference.

After effecting delivery of exogenous DNA to recipient cells, the next steps generally concern identifying the transformed cells for further culturing and plant regeneration. In practice DNA is introduced into only a small percentage of target cells in any one experiment. Marker genes are used to provide an efficient system for identification of those cells that are stably transformed by receiving and integrating a transgenic DNA construct into their genomes. Preferred marker genes provide selective markers which confer resistance to a selective agent, such as an antibiotic or herbicide. Potentially transformed cells are exposed to the selective agent. In the population of surviving cells will be those cells where, generally, the resistance-conferring gene has been integrated and expressed at sufficient levels to permit cell survival.

Cells may be tested further to confirm stable integration of the exogenous DNA. Useful selective marker genes include those conferring resistance to antibiotics such as kanamycin (nptII), hygromycin B (aph IV) and gentamycin (aac3 and aacC4) or resistance to herbicides such as glufosinate (bar or pat) and glyphosate (EPSPS; CP4). Examples of such selectable markers are illustrated in U.S. Pat. Nos. 5,550,318; 5,633,435; 5,780,708 and 6,118,047, all of which are incorporated herein by reference. Screenable markers which provide an ability to visually identify transformants can also be employed, e.g., a gene expressing a colored or fluorescent protein such as a luciferase or green fluorescent protein (GFP) or a gene expressing a beta-glucuronidase or uidA gene (GUS) for which various chromogenic substrates are known.

During transformation, exogenous DNA may be introduced randomly, i.e. at a non-specific location, in the plant genome. In some cases, it may be useful to target heterologous DNA insertion in order to achieve site-specific integration, e.g. to replace an existing gene in the genome. In some other cases it may be useful to target a heterologous DNA integration into the genome at a predetermined site from which it is known that gene expression occurs. Several site-specific recombination systems exist which are known to function in plants include Cre/lox as disclosed in U.S. Pat. No. 4,959,317 and FLP/FRT as disclosed in U.S. Pat. No. 5,527,695, both incorporated herein by reference.

Constructs and vectors may also include a transit peptide for targeting of a gene target to a plant organelle, particularly to a chloroplast, leucoplast or other plastid organelle. For a description of the use of a chloroplast transit peptide see U.S. Pat. No. 5,188,642, incorporated herein by reference.

VIII. Exogenous Genes for Modification of Plant Phenotypes

A particularly important advance of the present invention is that it provides methods and compositions for the efficient transformation of selected genes and regeneration of plants with desired agronomic traits. In this way, yield and other agronomic testing schemes can be carried out earlier in the commercialization process.

The choice of a selected gene for expression in a plant host cell in accordance with the invention will depend on the purpose of the transformation. One of the major purposes of transformation of crop plants is to add commercially desirable, agronomically important or end-product traits to the plant. Such traits include, but are not limited to, herbicide resistance or tolerance, insect resistance or tolerance, disease resistance or tolerance (viral, bacterial, fungal, nematode), stress tolerance and/or resistance, as exemplified by resistance or tolerance to drought, heat, chilling, freezing, excessive moisture, salt stress and oxidative stress, increased yield, food or feed content and value, physical appearance, male sterility, drydown, standability, prolificacy, starch quantity and quality, oil quantity and quality, protein quality and quantity, amino acid composition, and the like.

In certain embodiments of the invention, transformation of a recipient cell may be carried out with more than one exogenous (selected) gene. As used herein, an "exogenous coding region" or "selected coding region" is a coding region not normally found in the host genome in an identical context. By this, it is meant that the coding region may be isolated from a different species than that of the host genome, or alternatively, isolated from the host genome, but is operably linked to one or more regulatory regions which differ from those found in the unaltered, native gene. Two or more exogenous coding regions also can be supplied in a single transformation event using either distinct transgene-encoding vectors, or using a single vector incorporating two or more coding sequences. Any two or more transgenes of any description, such as those conferring herbicide, insect, disease (viral, bacterial, fungal, nematode) or drought resistance, male sterility, drydown, standability, prolificacy, starch properties, oil quantity and quality, or those increasing yield or nutritional quality may be employed as desired.

IX. Breeding Transgenic Plants of the Invention

In addition to direct transformation of a particular plant genotype, such as an elite line with enhanced transformability, with a construct prepared according to the current invention, transgenic plants may be made by crossing a plant having a construct of the invention to a second plant lacking the construct. For example, a selected coding region can be introduced into a particular plant variety by crossing, without the need for ever directly transforming a plant of that given variety. Therefore, the current invention not only encompasses a plant directly regenerated from cells which have been transformed in accordance with the current invention, but also the progeny of such plants. As used herein the term "progeny" denotes the offspring of any generation of a parent plant prepared in accordance with the instant invention, wherein the progeny comprises a construct prepared in accordance with the invention. "Crossing" a plant to provide a plant line having one or more added transgenes relative to a starting plant line, as disclosed herein, is defined as the techniques that result in a transgene of the invention being introduced into a plant line by crossing a starting line with a donor plant line that comprises a transgene of the invention. To achieve this one could, for example, perform the following steps:

(a) plant seeds of the first (starting line) and second (donor plant line that comprises a transgene of the invention) parent plants;

(b) grow the seeds of the first and second parent plants into plants that bear flowers;

(c) pollinate a flower from the first parent plant with pollen from the second parent plant; and (d) harvest seeds produced on the parent plant bearing the fertilized flower.

Backcrossing is herein defined as the process including the steps of:

(a) crossing a plant of a first genotype containing a desired gene, DNA sequence or element to a plant of a second genotype lacking said desired gene, DNA sequence or element;

(b) selecting one or more progeny plant containing the desired gene, DNA sequence or element;

(c) crossing the progeny plant to a plant of the second genotype; and (d) repeating steps (b) and (c) for the purpose of transferring said desired gene, DNA sequence or element from a plant of a first genotype to a plant of a second genotype.

Introgression of a DNA element into a plant genotype is defined as the result of the process of backcross conversion. A plant genotype into which a DNA sequence has been introgressed may be referred to as a backcross converted genotype, line, inbred, or hybrid. Similarly a plant genotype lacking said desired DNA sequence may be referred to as an unconverted genotype, line, inbred, or hybrid.

X. Definitions

Agronomically Elite:

Plants exhibiting desired agronomic traits are considered to be agronomically elite. Traits that may be considered to confer elitism include good seed set, good pollen set, excellent roots, good cold germination, good combining ability, tolerance to pests, tolerance to disease, tolerance to drought, tolerance to salts or metals, floral timing, timing between anthesis and silking, good lodging, upright leaves, good ear height, a good percentage of kernel moisture, high yield as an inbred, high yield as a hybrid, good plant height, stiff stalk and the like.

Genetic Transformation:

A process of introducing a DNA sequence or construct (e.g., a vector or expression cassette) into a cell or protoplast in which that exogenous DNA is incorporated into a chromosome or is capable of autonomous replication.

Exogenous Gene:

A gene which is not normally present in a given host genome in the exogenous gene's present form In this respect, the gene itself may be native to the host genome, however, the exogenous gene will comprise the native gene altered by the addition or deletion of one or more different regulatory elements.

Expression:

The combination of intracellular processes, including transcription and translation undergone by a coding DNA molecule such as a structural gene to produce a polypeptide.

Expression Cassette:

A chimeric DNA molecule which is designed for introduction into a host genome by genetic transformation. Preferred expression cassettes will comprise all of the genetic elements necessary to direct the expression of a selected gene. Expression cassettes prepared in accordance with the instant invention will include a maize cytoplasmic glutamine synthetase $GS_{1-2}$ promoter.

Expression Vector:

A vector comprising at least one expression cassette.

Introgress:

The process of transferring genetic material from one genotype to another.

Obtaining:

When used in conjunction with a transgenic plant cell or transgenic plant, obtaining means either transforming a non-transgenic plant cell or plant to create the transgenic plant cell or plant, or planting transgenic plant seed to produce the transgenic plant cell or plant.

Progeny:

Any subsequent generation, including the seeds and plants therefrom, which is derived from a particular parental plant or set of parental plants.

Promoter:

A recognition site on a DNA sequence or group of DNA sequences that provides an expression control element for a structural gene and to which RNA polymerase specifically binds and initiates RNA synthesis (transcription) of that gene.

$R_0$ Transgenic Plant:

A plant which has been directly transformed with a selected DNA or has been regenerated from a cell or cell cluster which has been transformed with a selected DNA.

Regeneration:

The process of growing a plant from a plant cell (e.g., plant protoplast, callus or explant).

Selected DNA:

A DNA segment which one desires to introduce into a plant genome by genetic transformation.

Selected Gene:

A gene which one desires to have expressed in a transgenic plant, plant cell or plant part. A selected gene may be native or foreign to a host genome, but where the selected gene is present in the host genome, will include one or more regulatory or functional elements which differ from native copies of the gene.

Transformation Construct:

A chimeric DNA molecule which is designed for introduction into a host genome by genetic transformation. Preferred transformation constructs will comprise all of the genetic elements necessary to direct the expression of one or more exogenous genes. Transformation constructs prepared in accordance with the instant invention will include a maize $GS_{1-2}$ promoter. In particular embodiments of the instant invention, it may be desirable to introduce a transformation construct into a host cell in the form of an expression cassette.

Transformed Cell:

A cell the DNA complement of which has been altered by the introduction of an exogenous DNA molecule into that cell.

Transgene:

A segment of DNA which has been incorporated into a host genome or is capable of autonomous replication in a host cell and is capable of causing the expression of one or more cellular products. Exemplary transgenes will provide the host cell, or plants regenerated therefrom, with a novel phenotype relative to the corresponding non-transformed cell or plant. Transgenes may be directly introduced into a plant by genetic transformation, or may be inherited from a plant of any previous generation which was transformed with the DNA segment.

Transgenic Plant:

A plant or progeny plant of any subsequent generation derived therefrom, wherein the DNA of the plant or progeny thereof contains an introduced exogenous DNA segment not originally present in a non-transgenic plant of the same strain.

The transgenic plant may additionally contain sequences which are native to the plant being transformed, but wherein the "exogenous" gene has been altered in order to alter the level or pattern of expression of the gene.

Transit Peptide:

A polypeptide sequence which is capable of directing a polypeptide to a particular organelle or other location within a cell.

Vector:

A DNA molecule capable of replication in a host cell and/or to which another DNA segment can be operatively linked so as to bring about replication of the attached segment. A plasmid is an exemplary vector.

XI. Deposit Information

A representative deposit of 2500 seeds of the corn variety designated 178-187-20 has been made with the American Type Culture Collection (ATCC), 10801 University Blvd., Manassas, Va. on May 8, 2003. Those deposited seeds have been assigned ATCC Accession NoPTA-5183.

A representative deposit of 2500 seeds of the corn variety designated 178-74-25 has been made with the American Type Culture Collection (ATCC), 10801 University Blvd., Manassas, Va. on May 8, 2003. Those deposited seeds have been assigned ATCC Accession No. PTA-5182.

The foregoing deposits were made in accordance with the terms and provisions of the Budapest Treaty relating to deposit of microorganisms and were made for a term of at least thirty (30) years and at least five (05) years after the most recent request for the furnishing of a sample of the deposits is received by the depository, or for the effective term of the patent, whichever is longer, and will be replaced if it becomes non-viable during that period.

XII. Examples

The following examples are included to illustrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

The current inventors have demonstrated a method and composition for the generation of elite maize lines with increased transformability. Maize lines Hi-II and FBLL were subjected to several rounds of marker assisted backcrossing, with FBLL as the recurrent female parent, concomitant with testing for enhanced culturability, regenerability, transformability and agronomic properties. Progeny lines showing increased transformability and good agronomic characteristics were selfed for several generations with continued testing for transformability. RFLP, SSR and SNP markers were applied to these lines and showed that five regions or QTLs associated with chromosomes 1, 3, 6 and 10 were associated with the enhanced transformability phenotype. Analysis of hybrids made with these increased transformability elite lines showed that yield was not significantly affected relative to commercially desired yield levels. The maize lines exhibiting enhanced transformability generated by the marker assisted breeding of FBLL and Hi-II according to the present invention as also referred to as FBLL-MAB lines.

Example 1

Marker Assisted Breeding of Enhanced Transformability into an Elite Maize Line

Parental lines Hi-II and FBLL were used in an initial breeding scheme. Hi-II had been previously identified to be culturable and regenerable (Armstrong et al., 1991; Armstrong et al., 1992) as well as transformable (Armstrong et al., 1995; Songstad, 1996; EP 0 586 355 A2), although it demonstrated poor agronomic qualities such as uneven ear formation, open-leaf plant architecture and non-uniformity in breeding. In contrast, elite inbred line FBLL does not initiate a sustainable callus culture and was found to perform poorly in transformation experiments; FBLL does, however, exhibit superior agronomic traits such as high yield, upright leaves, excellent roots, good cold germination and is of the stiff stalk heterotic group.

F1 progeny were produced by crossing FBLL and Hi-II. Hi-II was used as the male line and FBLL was used as the female line for the first cross (see FIG. 1). Using FBLL as the female parent, progeny of the first cross (F1) were backcrossed to FBLL to generate the BC1 generation. BC1 immature embryos were excised and cultured (see Example 2) and of these, about 9% of the embryos produced sustainable and regenerable embryogenic callus. Over 250 plants were regenerated from independent BC1 cultures.

RFLP analysis of leaf samples from the regenerated plants utilizing 96 polymorphic markers suggested that 6 regions were involved in the culturability and regenerability of the lines (Table 1). The regenerated samples emanated from a selected sample of cell lines showing a high degree of desirable type II callus, and, consequently, could be assumed to carry a high frequency of alleles for production of type II callus, and, hence, regenerability. At loci showing no effects from selection, the expected frequency of FBLL/FBLL homozygotes would be 50% in the backcross population; whereas, at loci showing significant effects from selection, the expected frequency of FBLL/FBLL homozygotes would be somewhat less than 50%. Markers showing a significant deviation of FBLL/FBLL homozygotes from 50% could be assumed, then, to be linked to QTL for regenerability. Markers for which the frequency of FBLL/FBLL homozygotes deviated significantly from 50% (with a probability of type I (false positive) error of less than 5% by the cumulative binomial distribution) were identified.

Marker analysis indicated that two unlinked regions on both the long and short arms of chromosome 1 as well as single regions on chromosomes 2, 3, 6, 10 were selected in the regenerable cultures for the observed tissue responses. Markers on chromosomes 1, 2 and 3 are similar to the regions found by Armstrong et al. (1992). Armstrong reported that a region on chromosome 9 was likely to be important for culturability and regenerability. The RFLP analysis carried out herein on the BC1 progeny did not identify any markers associated with enhanced transformability on chromosome 9. The RFLP markers in Table 1 herein, define six chromosomal regions related to culturability; these markers are publicly available.

Enzyme and probe information can be found in Table 10 (information obtained from the Maize Database at www.agron.missouri.edu).

TABLE 1

RFLP markers identified as important for culturability (BC1 generation tissue)

| Region | Chromosome | Marker 1 | Bin | Marker 2 | Bin |
|---|---|---|---|---|---|
| 1 | 1S* | npi234a | 1.03 | umc45 | 1.04 |
| 2 | 10 | npi254a | 10.04 | umc44a | 10.06 |

TABLE 1-continued

RFLP markers identified as important for culturability (BC1 generation tissue)

| Region | Chromosome | Marker 1 | Bin | Marker 2 | Bin |
|---|---|---|---|---|---|
| 3 | 3 | npi328b | 3.06 | npi212a | 3.07 |
| 4 | 2 | umc122a | 2.06 | | |
| 5 | 6 | npi373 | 6.02 | npi223a | 6.04 |
| 6 | 1L* | bn18.10a | 1.09 | npi615 | 1.09 |

*S = short arm of the chromosome; L = long arm of the chromosome

Plants regenerated from tissue culture were used as the male parent to backcross to the recurrent FBLL female inbred parent to produce the BC2 generation. Alternatively, plants regenerated from tissue culture were used as the female parent to backcross to FBLL to produce the BC2 generation. Due to the low likelihood of recovering a single progeny plant with all six identified QTL regions, two lines were selected, each with at least three different chromosomal regions of the six identified. Five BC2 ears each were designated to be lines "A" and "B." The ears were chosen based upon marker analysis for culturability regions and for the absence of chromosomal regions of Hi-II that were not linked to culturability. Line A was selected to have at least the markers for QTLs from chromosomes 1, 3 and 10. Line B was selected to have at least the markers for QTLs from chromosomes 2, 6, and the remaining unlinked marker on chromosome 1. Lines A and B were backcrossed to FBLL to generate the BC3 generation.

Marker analysis of the BC3 generation was carried out using polymorphic microsatellite markers (or SSRs), as well as RFLP markers. To confirm that the RFLP and SSR markers identified similar regions for culturability, DNA from the BC1 generation was re-analyzed with the same polymorphic SSR markers as the DNA from the BC3 generation. Marker screens on the parental FBLL and Hi-H lines were also carried out. Results from the analysis showed that approximately 2 to 4 SSR markers were found for each RFLP marker previously identified, however, the SSR data confirmed 5 of the 6 regions identified by RFLP (Table 2). Microsatellite markers did not reconfirm the region on chromosome 2 that was identified by Armstrong et al. (1992) or with RFLP marker U122 (Table 1). In addition, a single SSR marker identified a new region on chromosome 8. Chromosomes identified by fewer than two SSR markers, such as chromosomes 2 and 8, were not followed as enhanced transformability regions in the mapping of future generations. The SSR markers identified in Table 2 below are known to those of skill in the art and sequences for the primers used in the amplification of these SSR markers are in SEQ ID NOS:1-32, Table 11. (information obtained from the Maize Database at www.agron.missouri.edu).

TABLE 2

Microsatellite markers (SSRs) in regions important for culturability (BC3 generation tissue).

| Region | Chromosome | Marker 1 | Bin | Marker 2 | Bin | Marker 3 | Bin | Marker 4 | Bin |
|---|---|---|---|---|---|---|---|---|---|
| 1 | 1S | bnlg1484 | 1.04 | bnlg 1016 | 1.05 | bnlg 1811 | 1.05 | bnlg 1057 | 1.06 |
| 2 | 10 | bnlg 1450 | 10.07 | bnlg 1360 | 10.07 | | | | |
| 3 | 3 | bnlg 1605 | 3.07 | bnlg 1035 | 3.05 | bnlg 1160 | 3.06 | bnlg 1798 | 3.06 |
| 4 | 2 | none | | | | | | | |
| 5 | 6 | nc009 | 6.03 | bnlg 2249 | 6.04 | | | | |
| 6 | 1L | bnlg 1556 | 1.1 | bnlg 1564 | 1.09 | DUPSSR12 | 1.08 | | |
| 7 | 8 | bnlg 1350b | 8.06 | | | | | | |

In order to combine all 6 QTLs together within single plants, progeny from the BC3 generation were crossed with sibling BC3 plants ("sib" pollinated or "sibbed") or alternatively, self pollinated, to produce the BC3F1 generation. Two ears containing all five of the identified regions were harvested 12-13 days after pollination and cultures were initiated from the immature embryos. Approximately 5% of the embryos produced a callus response that could be maintained and regenerated. The resultant plants had the characteristic upright leaves of FBLL, and were taller and sturdier than the Hi-II parental controls.

SSR marker analysis indicated that four different BC3F1 lines contained five putative enhanced transformation QTLs (chromosomes 1S, 1L, 3, 6 and 10), at least in a heterozygous state. The four lines were designated 178-74, 178-187, 178-270 and 125-2. These lines were used for transformation testing. It is important to note that for any given generation used in a cross, the resulting embryos of that cross are of the next generation. For example, a cross between two F1 plants results in F2 embryos available for isolation.

Progeny of the BC3F1 generation were self- or sib-pollinated to produce the BC3F2 generation and the resultant immature BC3F2 embryos were assayed for transformability. The embryos were subjected to particle bombardment followed by glyphosate selection or to Agrobacterium-mediated transformation followed by kanamycin selection using the methods described in Examples 4 and 5. The vector used for glyphosate selection comprised a glyphosate resistant EPSPS gene operably linked to a 35S The vector used for NPTII selection comprised a neomycin phosphotransferase II selectable marker gene operably linked to a 35S promoter (Odell et al., 1985)). Both experiments produced transformed calli which were regenerated into mature transgenic maize plants in the greenhouse (Table 3; see Examples 4 and 5).

TABLE 3

Summary of FBLLxHiII transformation experiments
(BC3F1 generation; BC3F2 embryos)

| Selectable Marker | Transformation Method | Experiment # | Construct (pMON#) | # Bombed/ Inoculated | # Events Regenerating Plants |
|---|---|---|---|---|---|
| CP4 | Particle Bombardment | 367 | 36190 | 150 | 3 |
| NPTII | Agrobacterium | 385 | 18365 | 175 | 1 |

BC3F2 seed from plants at least heterozygous for all culturability regions was planted and genomic DNA was analyzed using SSRs. Plants with all or most of the 5 culturability QTLs were self-pollinated or sib pollinated to other BC3F2 plants to provide seed for the BC3F3 generation. Immature embryos were isolated from sib-pollinated BC3F3 plants to assay for transformability. Production of transformants is summarized in Tables 4 and 5. The vector used for kanamycin selection comprised a neomycin phosphotransferase II selectable marker gene operably linked to a 35S promoter. The vector used for glyphosate selection comprised a glyphosate resistant EPSPS gene operably linked to a rice actin 1 intron 1 promoter

TABLE 4

Agrobacterium-mediated transformation of FBLLxHi-II
using kanamycin selection and construct
pMON61334 (BC3F2 parents; BC3F3 embryos).

| Experiment # | FBLL-MAB Genotype[a] | #I.E.* Inoculated | #Events to GH | Transformation Efficiency (% TE) |
|---|---|---|---|---|
| 656 | 125-88 × 178-74 | 198 | 7 | 3.5 |
| 657 | 125-273 × 125-249 | 252 | 1 | 0.4 |
| 658 | 125-176 × 125-174 | 178 | 2 | 1.1 |
| 659 | 125-11 × 178-74 | 178 | 1 | 0.5 |
| 662 | 178-62 × 125-174 | 117 | 2 | 2.5 |
| 663 | 125-222 × 125-249 | 208 | 2 | 1.0 |
| 668 | 125-100 × 125-60 | 207 | 1 | 0.5 |
| 669 | 178-29 × 125-60 | 165 | 0 | — |
| 685 | 125-278 × 125-267 | 231 | 14 | 5.2 |
| 686 | 125-246 × 178-74 | 118 | 3 | 2.5 |
| 693 | 125-79 × 125-60 | 52 | 0 | — |
| 713 | 125-182 × 125-60 | 129 | 8 | 6.2 |
|  | Overall FBLL × Hi-II. | 2033 | 41 | 2.0% |
| 647 | Hi-II | 219 | 3 | 1.4 |
| 648 | Hi-II | 182 | 6 | 3.2 |
| 664 | Hi-II | 122 | 6 | 4.9 |
|  | Overall Hi-II. | 523 | 15 | 2.9% |

*I.E. = immature embryos

TABLE 5

Agrobacterium-mediated transformation of
FBLLxHi-II with glyphosate selection
using pMON61332 (BC3F2 parents; BC3F3 embryos).

| Experiment. # | # I.E. Inoculated | # Events to Greenhouse | % TE |
|---|---|---|---|
| 670 | 147 | 1 | 0.7 |
| 671 | 197 | 14 | 7.1 |
| 674 | 150 | 0 | 0 |
| 692 | 103 | 2 | 1.9 |
| Average | | | 2.4 |

SSR analysis was used to identify BC3F3 plants that were homozygous for the 5 regions and based upon this analysis, seven plant lines were selected for self pollination to fix the culturability and enhanced transformability QTLs: 178-74-25, 178-74-39, 178-187-8, 178-187-20, 178-270-18, 178-270-46, 125-2-1. Four of the seven lead lines contain all five of the regions identified while three lines lack the markers associated with chromosome 10.

Further self-crossing was carried out using these lead lines. SSR analysis was used to identify BC3F4 plants that were homozygous for the 5 regions on chromosomes 1, 3, 6 and 10, and the fixedness of the lines at these alleles is reported in Table 6. Select lines from the BC3F4 and BC3F5 generations resulting from these crosses were tested for transformation using glyphosate selection (see Example 5 for selection and regeneration information) and the results are shown in Table 7 and Table 8. The vector used for glyphosate selection comprised a glyphosate resistant EPSPS gene operably linked to a rice actin 1 intron 1 promoter.

TABLE 6

Genotype of fixed lead FBLLxHi-II lines with SSR markers (BC3F4 plant).

| FBLL-MAB Line | Allele at Chromosome Position | | | | | | | | | | | | |
|---|---|---|---|---|---|---|---|---|---|---|---|---|---|
|  | 1S 78[b] | 1S 103 | 1S 110 | 1L 139 | 1L 180 | 1L 202 | 3 85 | 3 103 | 3 112 | 6 61 | 6 65 | 10 125 | 10 124 |
| 178-74-25 | 2[a] | 2 | 2 | 2 | 2 | 2 | 1 | 2 | 2 | 2 | 2 | 2 | 2 |
| 178-74-39 | 2 | 2 | 2 | 2 | 2 | 2 | 1 | 2 | 2 | 2 | 2 | 1 | 1 |
| 178-187-8 | 2 | 2 | 1 | 1 | 2 | 2 | 1 | 2 | 1 | 2 | 2 | 1 | 1 |
| 178-187-20 | 2 | 2 | 1 | 1 | 2 | 2 | 1 | 2 | 2 | 2 | 2 | 1 | 1 |
| 178-270-18 | 2 | 2 | 2 | 2 | 2 | 2 | 1 | 2 | 2 | 2 | 2 | 2 | 2 |

TABLE 6-continued

Genotype of fixed lead FBLLxHi-II lines with SSR markers (BC3F4 plant).

| FBLL-MAB Line | Allele at Chromosome Position | | | | | | | | | | | | |
|---|---|---|---|---|---|---|---|---|---|---|---|---|---|
| | 1S 78[b] | 1S 103 | 1S 110 | 1L 139 | 1L 180 | 1L 202 | 3 85 | 3 103 | 3 112 | 6 61 | 6 65 | 10 125 | 10 124 |
| 178-270-46 | 2 | 2 | 1 | 2 | 2 | 2 | 1 | 2 | 2 | 2 | 2 | 2 | 2 |
| 125-2-1 | 2 | 2 | 1 | 1 | 2 | 2 | 2 | 2 | 1 | 2 | 2 | 2 | 2 |

[a]1 = FBLL and 2 = A188
[b]position on chromosome: corresponding SSR marker. 78: bnlg1484; 103: bnlg1016; 110: bnlg1811; 139: bnlg1042; 180: DUPSSR12; 202: bnlg1556; 85: bnlg1035; 103: bnlg1160; 112: bnlg1605; 61: nc009; 65: bnlg2245; 125: bnlg1450; 124: bnlg1360.

TABLE 7

*Agrobacterium*-mediated transformation of FBLLxHi-II maize lines with pMON70801 and glyphosate selection (BC3F3 parents; BC3F4 embryos).

| FBLLxHi-II line | # I.E.s inoculated | Average % TE | Standard Deviation |
|---|---|---|---|
| 178-74 | 887 | 2.9 | 2.7 |
| 178-187 | 2640 | 2.4 | 5.2 |
| Overall | 3527 | 2.6 | 4.4 |

TABLE 8

*Agrobacterium*-mediated transformation of FBLLxHi-II maize lines with pMON70801 and glyphosate selection (BC3F4 parents; BC3F5 embryos).

| FBLLxHi-II line | Avg. # I.E.s per ear | # of Expts. | # I.E.s inoculated | Average * % TE |
|---|---|---|---|---|
| 178-187-20 | 186 | 5 | 821 | 5.45 |
| 178-74-25 | 189 | 6 | 1604 | 5.12 |
| 178-74-39 | 160 | 9 | 1579 | 1.45 |
| 178-187-8 | 188 | 2 | 485 | 8.72 |
| 125-2-1 | 207 | 1 | 410 | 6.83 |
| 178-270-46 | 211 | 1 | 124 | 1.61 |

* transformed callus, not fully regenerated plants
na—no standard deviation available as only one experiment was carried out Two lines were selected as having increased transformability in an elite female maize germplasm with desirable agronomic characteristics: 178-187-20 and 178-74-25. These lines exhibited good seed set and were shown to provide an average of 186 to 189 immature embryos per ear (Table 8). The lines showed good agronomic characteristics in the field and greenhouse including upright leaves, stiff stalk and a tassel with improved pollen shed over the starting FBLL parent. The lines were fixed for four culturability/enhanced transformability QTLs on chromosomes 1, 3 and 6; line 178-24-25 also contained the region from chromosome 10. In addition, it was observed that each line also contain unselected regions on chromosomes 4 and 8 derived from the elite parent, FBLL.

Marker analysis using 172 polymorphic SNPs covering 88-89% of the genome (Table 9) indicated that line 178-74-25 was 82.9% FBLL in nature and 93.6% fixed for all markers tested. Line 178-187-20 was identified to be 81.7% FBLL in nature and 99.4% fixed for all markers tested. One of skill in the art would realize that any type of molecular marker such as RFLP, SSR or SNP could be used to determine the fixedness or genetic fingerprint of any corn line for a given set of regions or QTLs. Table 12 indicates the locations of the polymorphic SNPs used in the study.

TABLE 9

SNP fingerprint analysis of FBLLxHi-II (BC3F5 generation tissue)

| FBLLxHi-II line | Extent (%) of FBLL conversion | % Homozygosity for markers |
|---|---|---|
| 178-74-25 | 82.9 | 93.6 |
| 178-74-39 | 83.8 | 97.1 |
| 178-187-8 | 84.4 | 98.8 |
| 178-187-20 | 81.7 | 99.4 |
| 178-270-18 | 87.9 | 94.8 |
| 178-270-46 | 87.1 | 98.3 |

Average transformation efficiencies for lines 178-187-20 and 178-74-25 were found to be approximately 5.28% and transformation efficiencies of up to 14% were achieved in individual experiments (average for 178-74-25 was 5.12%; average for 178-187-20 was 5.45%). Hi-II transformation efficiencies are typically in the 5% to 30% range. Under the conditions used to assay for transformability of the FBLLxHi-II lines, no parental FBLL transfomants were recovered. The data presented above indicate that using the breeding and testing methods employed herein, genomic regions were transferred from Hi-II to elite female line FBLL that allowed for enhanced transformability in a female inbred with desirable agronomic properties.

Example 2

Culturing Immature Embryos from FBLLxHi-II and Plant Regeneration

At various points in the introgression of the increased transformability QTLs into FBLL, immature embryos were isolated for culturability and transformation testing. Embryos were isolated from ears approximately 10 to 14 days after pollination, preferably 12 days after pollination, and placed onto 211V media (1×N6 basal salts, 1 mg/L 2,4-dichlorophenoxyacetic acid (2-4,D); 1 mg/L thiamine; 0.5 mg/L nicotinic acid; 0.91 g/L L-asparagine monohydrous; 100 mg/L myo-inositol; 0.5 g/L 2-(4-morpholino)-ethane sulfonic acid (MES); 1.6 g/L MgCL2.6H2O; 100 mg/L casein hydrolysate; 0.69 g/L proline; 20 g/L sucrose; pH to 5.8; 16.9 mg/L silver nitrate (letter code=V); solidified with 2 g/L Gelgro agar). The embryos remained on 211V media in the dark at approximately 28° C. for approximately 2 weeks before transfer to fresh 211 media (media 211V lacking silver nitrate). Transfers to fresh media were repeated approximately every 2 weeks for an additional 2 to 6 weeks, preferably 2 to 4 weeks, and callus formation was visually observed. Alternatively, embryos are excised onto 211 media for approximately 2 weeks in the dark at approximately 28° C., followed by transfers approximately every two weeks onto fresh 211 media.

Healthy, friable callus was selected from 211 media for generation into plantlets; friable callus is characterized by being soft and loose in terms of consistency. In one embodiment, callus on 211 media was placed onto 105 media (1×MS basal salts; 0.4 mg/L napthol acetic acid; 3 mg 6-benzylaminopurine (BAP); 1 mg/L thiamine; 0.5 mg/L nicotinic acid; 0.91 g/L L-asparagine monohydrous; 100 mg/L myo-inositol; 100 mg/L casein hydrolysate; 0.69 g/L proline; 20 g/L sorbitol; pH to 5.8; solidified with 2 g/L Gelgro) for approximately 2 weeks in the dark at approximately 28° C., followed by a transfer to fresh 105 media for an additional 2 weeks, the second week of which the regenerating plantlets were exposed to light. After approximately 2 to 4 weeks on the 105 regeneration media, plantlets were transferred to 110 media (0.5×MS basal salts; 0.5 mg/L thiamine; 0.5 mg/L nicotinic acid; 30 g/L sucrose; pH to 5.8; solidified with 3.6 g/L Gelgro) in deep dish containers (in the light at approximately 28° C.) and transferred to fresh 110 media in the appropriate container, such as PHYTATRAYS™ (plant cell culture vessel) or PLANTCONS® (plant cell culture vessel), approximately every 2 weeks until plantlets were regenerated, approximately 2-3 transfers. Plantlets with good root and shoot development were selected and placed into soil for development into mature plants. One of skill in the art would realize that the selection of media, growth supplements, times of transfer and other intricacies of plant tissue culture may vary yet result in the induction of callus formation and regeneration of a mature, fertile plant.

In another embodiment, plant regeneration involves placing the callus onto 217 media (1×N6 basal salts; 1 mg/L thiamine; 0.5 mg/L nicotinic acid; 3.52 mg/L BAP; 0.91 g/L L-asparagine monohydrate; 0.1 g/L myo-inositol; 0.5 g/L MES; 1.6 g/L MgCL2.6H2O; 100 mg/L casein hydrolysate; 0.69 g/L proline; 20 g/L sucrose; pH to 5.8; 16.9 mg/L silver nitrate; solidified with 2 g/L Gelgro agar) for approximately 1 week in the dark at approximately 28° C.; this incubation in the dark may be followed by a second week in the light. Healthy callus is transferred to 127 media (1×MS basal salts; 1×MS Fromm; 0.15 g/L L-asparagine; 0.1 g/L myo-inositol; pH to 5.8; 10 g/L glucose; 20 g/L maltose; solidified with 6 g/L Phytagar) and placed in the light at approximately 28° C. until plantlets formed. Alternatively, subsequent transfers to fresh 127 media are made approximately every 2 weeks until plantlets were regenerated, approximately 2-3 transfers. Plantlets with good root and shoot development were selected and placed into soil for development into mature plants.

Example 3

Molecular DNA Markers

The introgression of traits into plants such as maize may be monitored most easily by visual clues such as plant height, kernel color or plant morphology. For traits that are not easily observed by visual inspection, such as enhanced transformability, molecular markers may be used to monitor and breed for such desired traits. This type of introgression is often called marker assisted breeding or MAB. The maize lines exhibiting enhanced transformability generated by the marker assisted breeding described herein are designated as FBLL-MAB lines. Of particular interest to the present invention are three types of molecular markers: RFLP, SSR and SNP. One of skill in the art would realize that a variety of other markers exist and may be employed in MAB for a given trait or QTL.

A. RFLP Markers

RFLP markers as molecular tools and methods to employ the markers are well known in the art. The RFLP markers employed in the present invention are publicly available and are listed in Table 1. Table 10 indicates the restriction enzyme used in the RFLP mapping and the probes employed. (Probes are available to the public via G. Davis or T. Musket, 1-87 Agriculture Building, University of Missouri, Columbia, Mo. 65211; see also the Maize Database at www.agron.missouri.edu.)

TABLE 10

Restriction enzymes and RFLP probes.

| Chromosome | Marker 1 | Bin | Enzyme | Probe |
| --- | --- | --- | --- | --- |
| 1S | npi234a | 1.03 | HindIII | p-G20B-09 |
| 1S | umc45 | 1.04 | EcoRI | umc45 |
| 10 | npi254a | 10.04 | HindIII | p-G21B-02 |
| 10 | umc44a | 10.06 | HindIII | umc44 |
| 3 | npi328b | 3.06 | EcoRV | p-G1B-11 |
| 3 | npi212a | 3.07 | EcoRI | p-G1D-10 |
| 2 | umc122a | 2.06 | HindIII | umc122 |
| 6 | npi373 | 6.02 | HindIII | p-G22G-09 |
| 6 | npi223a | 6.04 | HindIII | p-G2B-08 |
| 1L | bnl8.10 | 1.09 | HindIII | bnl8.10 |
| 1L | npi615 | 1.09 | HindIII | p-G24F-04 |

B. SSR Markers

SSR markers are PCR based molecular marker and breeding tools that are known to those of skill in the art, as are the molecular methods of identification and analysis. A number of publicly available SSR markers have been identified and may be employed in the practice of the present invention (see for example the Maize Database www.agron.missouri.edu).

The SSR markers employed in the present invention are available to the public and primers used to amplify these markers are listed in Table 11 and in SEQ ID NOS:1-32.

TABLE 11

SSR markers and SEQ ID numbers for primers.

| Chromosome | Marker | Bin | Primer 1 | Primer 2 |
| --- | --- | --- | --- | --- |
| 1S | bnlg1484 | 1.04 | SEQ ID NO: 1 | SEQ ID NO: 2 |
| 1S | bnlg 1016 | 1.05 | SEQ ID NO: 3 | SEQ ID NO: 4 |
| 1S | bnlg 1811 | 1.05 | SEQ ID NO: 5 | SEQ ID NO: 6 |
| 1S | bnlg 1057 | 1.06 | SEQ ID NO: 7 | SEQ ID NO: 8 |
| 10 | bnlg 1450 | 10.07 | SEQ ID NO: 9 | SEQ ID NO: 10 |
| 10 | bnlg 1360 | 10.07 | SEQ ID NO: 11 | SEQ ID NO: 12 |
| 3 | bnlg 1605 | 3.07 | SEQ ID NO: 13 | SEQ ID NO: 14 |
| 3 | bnlg 1035 | 3.05 | SEQ ID NO: 15 | SEQ ID NO: 16 |
| 3 | bnlg 1160 | 3.06 | SEQ ID NO: 17 | SEQ ID NO: 18 |
| 3 | bnlg 1798 | 3.06 | SEQ ID NO: 19 | SEQ ID NO: 20 |
| 2 | none | | | |
| 6 | nc009 | 6.03 | SEQ ID NO: 21 | SEQ ID NO: 22 |
| 6 | bnlg 2249 | 6.04 | SEQ ID NO: 23 | SEQ ID NO: 24 |
| 1L | bnlg 1556 | 1.1 | SEQ ID NO: 25 | SEQ ID NO: 26 |
| 1L | bnlg 1564 | 1.09 | SEQ ID NO: 27 | SEQ ID NO: 28 |
| 1L | DUPSSR12 | 1.08 | SEQ ID NO: 29 | SEQ ID NO: 30 |
| 8 | bnlg 1350b | 8.06 | SEQ ID NO: 31 | SEQ ID NO: 32 |

C. SNP Markers

SNP markers as molecular tools and methods to employ these markers are known in the art. In the present invention, SNP markers were used to characterize the degree of homozygosity and conversion to the FBLL genotype. Oligonucleotide primers were designed to prime near or in regions of the genome that are characterized by small sequence variations such as a difference, an addition or a deletion in a single nucleotide. Various genotypes of maize may contain different but trackable differences in their genomes. Following DNA isolation and amplification of the target area, the differences in the amplified products were characterized by a number of molecular tools such as oligonucleotide hybridization, TaqMan, molecular beacons, sequencing or other detection methods. In a similar fashion to the RFLP and SSR analyses, the sequences of the amplification products of the progeny and parental lines were analyzed to determine the distribution of markers. A limited but growing number of publicly available SNP markers have been identified (Bhattramakki et al., 2000; Tenaillon et al., 2001).

The chromosomal locations of the SNP markers employed in the present invention are listed in Table 13. Table 10 reports the fixedness of each transformable FBLL line as determined by these SNP markers. One of skill in the art would recognize that any type of marker localizing to the chromosomal locations indicated in Table 12 would be useful in the practice of the present invention.

TABLE 12

Location of SNP markers.

| Chromosome | Location | SNP marker |
|---|---|---|
| 1 | 29 | NC0110473 |
| 1 | 38 | NC0028164 |
| 1 | 40 | NC0043230 |
| 1 | 51 | NC0108007 |
| 1 | 62 | NC0037716 |
| 1 | 62 | NC0043571 |
| 1 | 68 | NC0108891 |
| 1 | 75 | NC0029329 |
| 1 | 81 | NC0043554 |
| 1 | 83 | NC0004287 |
| 1 | 85 | NC0105022 |
| 1 | 88 | NC0029053 |
| 1 | 88 | NC0112443 |
| 1 | 96 | NC0066981 |
| 1 | 97 | NC0111854 |
| 1 | 121 | NC0033373 |
| 1 | 123 | NC0108100 |
| 1 | 132 | NC0009628 |
| 1 | 135 | NC0109882 |
| 1 | 189 | NC0008996 |
| 1 | 198 | NC0013490 |
| 1 | 198 | NC0030840 |
| 1 | 216 | NC0005177 |
| 2 | 6 | NC0009867 |
| 2 | 16 | NC0009766 |
| 2 | 16 | NC0033786 |
| 2 | 28 | NC0003388 |
| 2 | 31 | NC0014461 |
| 2 | 32 | NC0016074 |
| 2 | 35 | NC0080031 |
| 2 | 45 | NC0078243 |
| 2 | 69 | NC0019110 |
| 2 | 73 | NC0036323 |
| 2 | 76 | NC0011466 |
| 2 | 94 | NC0000366 |
| 2 | 94 | NC0059782 |
| 2 | 123 | NC0009639 |
| 2 | 126 | NC0009818 |
| 2 | 134 | NC0044031 |
| 2 | 155 | NC0110974 |
| 3 | 0 | NC0002719 |
| 3 | 0 | NC0051614 |
| 3 | 0 | NC0106276 |
| 3 | 5 | NC0106389 |
| 3 | 10 | NC0048700 |
| 3 | 24 | NC0009963 |
| 3 | 84 | NC0010933 |
| 3 | 90 | NC0108089 |
| 3 | 92 | NC0004735 |
| 3 | 102 | NC0011320 |
| 3 | 111 | NC0015965 |
| 3 | 116 | NC0036694 |

TABLE 12-continued

Location of SNP markers.

| Chromosome | Location | SNP marker |
|---|---|---|
| 3 | 123 | NC0108630 |
| 3 | 149 | NC0009079 |
| 3 | 169 | NC0014041 |
| 4 | 1 | NC0009523 |
| 4 | 1 | NC0012340 |
| 4 | 4 | NC0104957 |
| 4 | 13 | NC0002739 |
| 4 | 25 | NC0038293 |
| 4 | 32 | NC0110069 |
| 4 | 53 | NC0012012 |
| 4 | 60 | NC0070728 |
| 4 | 63 | NC0020481 |
| 4 | 68 | NC0003351 |
| 4 | 78 | NC0032557 |
| 4 | 78 | NC0040744 |
| 4 | 83 | NC0035625 |
| 4 | 85 | NC0003964 |
| 4 | 85 | NC0037540 |
| 4 | 85 | NC0107840 |
| 4 | 94 | NC0036240 |
| 4 | 98 | NC0108028 |
| 4 | 104 | NC0050947 |
| 4 | 110 | NC0110764 |
| 4 | 124 | NC0111514 |
| 4 | 130 | NC0051079 |
| 4 | 161 | NC0003224 |
| 5 | 12 | NC0004808 |
| 5 | 25 | NC0033977 |
| 5 | 30 | NC0020668 |
| 5 | 36 | NC0016527 |
| 5 | 51 | NC0009490 |
| 5 | 52 | NC0005169 |
| 5 | 55 | NC0019333 |
| 5 | 63 | NC0040571 |
| 5 | 69 | NC0013657 |
| 5 | 79 | NC0009297 |
| 5 | 82 | NC0003338 |
| 5 | 82 | NC0078477 |
| 5 | 86 | NC0008807 |
| 5 | 93 | NC0019634 |
| 5 | 93 | NC0112617 |
| 5 | 98 | NC0010131 |
| 5 | 148 | NC0113237 |
| 6 | 2 | NC0014417 |
| 6 | 8 | NC0077806 |
| 6 | 13 | NC0066735 |
| 6 | 35 | NC0108212 |
| 6 | 39 | NC0060751 |
| 6 | 40 | NC0055758 |
| 6 | 43 | NC0009134 |
| 6 | 46 | NC0003277 |
| 6 | 46 | NC0008833 |
| 6 | 56 | NC0070996 |
| 6 | 66 | NC0110972 |
| 6 | 71 | NC0019588 |
| 6 | 84 | NC0031684 |
| 6 | 101 | NC0053636 |
| 6 | 104 | NC0009667 |
| 6 | 110 | NC0021734 |
| 6 | 110 | NC0043724 |
| 7 | 0 | NC0058637 |
| 7 | 28 | NC0035408 |
| 7 | 49 | NC0070392 |
| 7 | 49 | NC0081460 |
| 7 | 56 | NC0009674 |
| 7 | 56 | NC0018565 |
| 7 | 56 | NC0079307 |
| 7 | 70 | NC0009872 |
| 7 | 72 | NC0017039 |
| 7 | 93 | NC0028273 |
| 7 | 105 | NC0011659 |
| 7 | 107 | NC0106258 |
| 8 | 0 | NC0024672 |
| 8 | 5 | NC0019198 |
| 8 | 7 | NC0038724 |
| 8 | 11 | NC0040299 |

TABLE 12-continued

Location of SNP markers.

| Chromosome | Location | SNP marker |
|---|---|---|
| 8 | 24 | NC0008934 |
| 8 | 24 | NC0034552 |
| 8 | 24 | NC0038939 |
| 8 | 31 | NC0005266 |
| 8 | 38 | NC0022765 |
| 8 | 43 | NC0082612 |
| 8 | 57 | NC0020514 |
| 8 | 70 | NC0082386 |
| 8 | 80 | NC0020546 |
| 8 | 86 | NC0004587 |
| 8 | 88 | NC0005592 |
| 8 | 103 | NC0016260 |
| 8 | 109 | NC0004171 |
| 8 | 115 | NC0014566 |
| 8 | 119 | NC0011309 |
| 9 | 0 | NC0014476 |
| 9 | 7 | NC0081558 |
| 9 | 14 | NC0002735 |
| 9 | 38 | NC0041796 |
| 9 | 49 | NC0112139 |
| 9 | 51 | NC0008935 |
| 9 | 51 | NC0018302 |
| 9 | 51 | NC0029744 |
| 9 | 54 | NC0031039 |
| 9 | 58 | NC0002611 |
| 9 | 58 | NC0021430 |
| 9 | 58 | NC0112189 |
| 9 | 66 | NC0014826 |
| 9 | 66 | NC0110125 |
| 9 | 73 | NC0021860 |
| 9 | 73 | NC0042348 |
| 9 | 78 | NC0009555 |
| 9 | 86 | NC0028507 |
| 9 | 91 | NC0020368 |
| 9 | 104 | NC0042929 |
| 9 | 117 | NC0077194 |
| 10 | 32 | NC0008956 |
| 10 | 55 | NC0081776 |
| 10 | 60 | NC0033664 |
| 10 | 64 | NC0011115 |
| 10 | 65 | NC0036251 |
| 10 | 69 | NC0067173 |
| 10 | 82 | NC0008643 |
| 10 | 86 | NC0008756 |

Example 4

Bombardment of FBLL×Hi-II BC3F2 Immature Embryos, Glyphosate Selection and Plant Regeneration Many variations in techniques for microprojectile bombardment are well known in the art and therefore deemed useful with the current invention.

A. Preparation of Microprojectiles

Microprojectiles were prepared for use with the electric discharge particle acceleration gene delivery device (U.S. Pat. No. 5,015,580) by suspending 20 mg of 0.6 µm gold particles (BioRad) in 100 µl buffer (150 mM NaCl, 10 mM Tris-HCl, pH 8.0). Using standard molecular biology techniques, a cassette was isolated from pMON36190 comprising a rice actin promoter:cre recombinase coding sequence:35S promoter:CP4 coding sequence. Approximately 1.56 mg of cassette DNA isolated from pMON36190 was added to the suspension of gold particles and gently vortexed for about five seconds. One of skill would realize that the amount of DNA used as well as the amount and volume of microprojectiles prepared for use in particle transformation may vary. For example, one might use about 2 to 2000 ng, preferably about 2 to 1500 ng, more preferably 2 to 1000 ng, more preferably 2 to 750 ng, more preferably 2 to 500 ng, or more preferably 2 to 250 ng of DNA per particle preparation.

One hundred and fifty µl of 0.1M spermidine was added and the solution vortexed gently for about 5 seconds. One hundred and fifty µl of a 25% solution of polyethylene glycol (3000-4000 molecular weight, American Type Culture Collection) was added and the solution was gently vortexed for five seconds. One hundred and fifty µl of 2.5 M $CaCl_2$ was added and the solution vortexed for five seconds. Following the addition of $CaCl_2$, the solution was incubated at room temperature for 10 to 15 minutes. The suspension was subsequently centrifuged for 20 seconds at 12,000 rpm and the supernatant discarded. The gold particle/DNA pellet was washed twice with one ml 100% ethanol and resuspended to a total volume of 20 ml in 100% ethanol. The gold particle/DNA preparation was stored at −20° C. for up to two weeks.

DNA was introduced into maize cells using the electric discharge particle acceleration gene delivery device (U.S. Pat. No. 5,015,580). The gold particle/DNA suspension was coated on Mylar sheets (Du Pont Mylar polyester film type SMMC2, aluminum coated on one side, over coated with PVDC co-polymer on both sides, cut to 18 mm square) by dispersion of 310 to 320 µl of the gold particle/DNA suspension on a sheet. After the gold particle suspension settled for one to three minutes, excess ethanol was removed and the sheets were air dried. Microprojectile bombardment of maize tissue was conducted as described in U.S. Pat. No. 5,015,580. AC voltage may be varied in the electric discharge particle delivery device. For microprojectile bombardment of Hi-II, FBLL or Hi-II×FBLL pre-cultured immature embryos, 30% to 40% of maximum voltage was preferably used. Following microprojectile bombardment, tissue was cultured in the dark at 27° C.

B. Bombardment and Selection

A rice actin promoter:cre recombinase coding sequence: 35S promoter:CP4 coding sequence fragment was isolated from vector pMON36190 using standard molecular biology techniques, and introduced into FBLL×Hi-II BC3F2 immature embryos. Maize immature embryos of approximately 1.8 mM were isolated 12 days post-pollination from greenhouse grown plants that had been self or sib pollinated; those of skill would know that embryos of 1.2-3.0 mM and harvested 10-14 days post-pollination are also useful. Immature embryos were cultured on 211V medium in the dark at approximately 27° C. Immature embryos were bombarded 5 days after isolation although one of skill in the art would recognize that embryos may be bombarded 0 to 6 days post-excision. Prior to bombardment, the immature embryos were transferred to 211 medium containing 12% sucrose (211 SV) for 4 hours, although 3-6 hours may also be employed. Following bombardment, tissue cultures were incubated overnight and transferred to 211V. After approximately 1 week on 211V, cultures were transferred to media 211JV (media 211V with 1 mM glyphosate). After approximately 2 weeks, callus was transferred to fresh selection medium; approximately half of the cultures were placed onto fresh 211J media (211 with 1 mM glyphosate) while the remaining cultures were placed onto fresh 211K media (211 with 3 mM glyphosate). After approximately 4 weeks on 211J or 211K, cultures were transferred to fresh 211K media. Approximately 2 weeks post-transfer, all putative events were transferred to fresh 211K media followed by subsequent culturing for plant regeneration.

C. Regeneration of Fertile Transgenic Plants

Fertile transgenic plants were produced from transformed FBLL×Hi-II BC3F2 maize cells. Transformed callus was transferred from selection medium to maturation medium 105 and held for approximately 2 weeks in the dark at 26°-28° C., whereupon somatic embryos mature and shoot regeneration begins. Following approximately 2 weeks on 105 media, the regenerating tissue was transferred to fresh 105 media in the light for an additional 2 weeks. Tissue was transferred to medium 110 and allowed to regenerate further for another 3 to 5 weeks before transplantation to soil. One of skill in the art would know that the amount of time a regenerated callus or tissue is exposed to a given media will vary with the condition of the tissue, type of media and other factors that affect tissue culture conditions.

The results from the microprojectile bombardment of FBLLxHi-II BC3F2 immature embryos show that a transformation efficiency of approximately 2% was achieved. This represents an improvement over the TE for FBLL, from which under the conditions employed herein no transformants were recovered, and is more comparable to the TE for Hi-II, which is typically in the range of 5 to 30%.

Example 5

Transformation of Maize FBLLxHi-II BC3F2, BC3F4 and BC3F5 Immature Embryos Using *Agrobacterium tumefaciens*

Methods of *Agrobacterium* mediated transformation of maize cells and other monocots are known (Hiei et al., 1997; U.S. Pat. No. 5,591,616; U.S. Pat. No. 5,981,840; published EP patent application EP 0 672 752). Although various strains of *Agrobacterium* may be used (see references above), strain ABI was used by the present inventors. The ABI strain of *Agrobacterium* was derived from strain A208, a C58 nopaline type strain, from which the Ti plasmid was eliminated by culture at 37° C., and further containing the modified Ti plasmid pMP90RK (Koncz and Schell, 1986). An *Agrobacterium tumefaciens* binary vector system (An et al., 1998) was used to transform maize. Alternative cointegrating Ti plasmid vectors have been described (Rogers et al., 1988) and could be used to transform maize. A binary vector may contain a selectable marker gene, a screenable marker gene and/or one or more genes that confer a desirable phenotypic trait on the transformed plant. Many types of binary vectors may be used and are known to those of skill in the art.

Vector pMON18365 was introduced into a disarmed *Agrobacterium* strain using electroporation (Wen-jun and Forde, 1989); alternatively triparental mating (Ditta et al., 1980) may be employed to introduce DNA into the bacterium. *Agrobacterium* cells were grown at 28° C. in LB (DIFCO) liquid medium comprising 100 µg/ml each streptomycin, kanamycin and spectinomycin as well as 25 µg/ml chloramphenicol to select for maintenance of the modified Ti plasmid and binary vector. It will be obvious to one of skill in the art to use appropriate selection agents at the appropriate concentrations to maintain plasmids in the host *Agrobacterium* strain.

Prior to inoculation of BC3F2 maize cells, *Agrobacterium* cells containing vector pMON18365 were grown overnight at room temperature in AB medium (Chilton et al., 1974) comprising 50 µg/ml each streptomycin, kanamycin and spectinomycin as well as 25 µg/ml chloramphenicol for plasmid maintenance and 200 uM acetosyringone. Immediately prior to inoculation of maize cells, *Agrobacterium* were preferably pelleted by centrifugation, washed in ½ MSVI medium (1.1 g/L GIBCO MS salts, 2 mg/L glycine, 0.5 g/L niacin, 0.5 g/L L-pyridoxine-HCl, 0.1 mg/L thiamine, 115 g/L L-proline, 10 g/L D-glucose, and 10 g/L sucrose, pH 5.4) containing 200 µM acetosyringone, and resuspended at 0.1 to 1.0×10$^9$ cells/ml in ½ MSPL medium (1.1 g/L GIBCO MS salts, 2 mg/L glycine, 0.5 g/L niacin, 0.5 g/L L-pyridoxine-HCl, 0.1 mg/L thiamine, 115 g/L L-proline, 26 g/L D-glucose, 68.5 g/L sucrose, pH 5.4) containing 200 µM acetosyringone. One of skill in the art may substitute other media for ½ MSPL.

Immature maize FBLLxHi-II BC3F2 embryos, approximately 1.5 to 2.0 mM in size, were isolated 12 days post-pollination. In one embodiment, embryos were actively isolated for 15 minutes and, as they were removed from the cob, placed immediately directly in a suspension of *Agrobacterium* containing vector pMON18365 (OD$_{660}$=1). After the 15 minutes of dissection was complete, the isolated embryos were allowed to incubate in the *Agrobacterium* suspension for an additional 5 minutes. In another embodiment, embryos were actively isolated for 25 minutes and, as they were removed from the cob, placed immediately directly in a suspension of *Agrobacterium* containing vector pMON18365 (OD$_{660}$=1). After the 25 minutes of dissection was complete, the isolated embryos were allowed to incubate in the *Agrobacterium* suspension for an additional 5 minutes. Following exposure to the *Agrobacterium*, the embryos were placed onto CC1-STS co-culture media (0.5×MS salts; 1×MS vitamins; 0.5 mg/L thiamine HCl; 0.115 g/L proline; 10 g/L glucose; 20 g/L sucrose; 3 mg/L 2,4-D; pH to 5.2; supplemented with 20 µM silver thiosulphate; 200 µM acetosyringone and solidified with 5.5 g/L low melt agarose) and incubated overnight at approximately 23° C.

Embryos were transferred from CC1-STS co-culture media to fresh 211NV media (211 media supplemented with 750 mg/L carbenicillin and 100 µM AgNO$_3$) for a delay incubation of approximately 5 days. Embryos were then transferred onto fresh 211RV media (211V with 500 mg/L carbenicillin) containing 50 mg/L kanamycin. A transfer onto fresh 211A media (211 media with 250 mg/L carbenicillin) containing 50 mg/L kanamycin was carried out after about 2 weeks. Approximately 2 weeks later, tissue was transferred to 211A supplemented with 100 mg/L kanamycin. Approximately 2 weeks after, tissue was transferred to 211 AF (211A with 200 mg/L kanamycin). A transfer from 211AF to fresh 211AF was repeated an additional 2 times. A GUS staining assay, known to those of skill in the art, was carried out on a bit of callus isolated after two passes on 211AF (Jefferson et al., 1986, Jefferson, 1987). Blue staining of the tissue indicated expression of the uidA gene and GUS product in the transformed elite FBLLxHi-II BC3F2 tissue.

After approximately 2 weeks on the third round of 211AF selection media, healthy, friable tissue was selected for regeneration. In one embodiment, tissue was transferred to 105 media in the dark. After approximately 2 weeks, the healthiest tissue on 105 was transferred to fresh 105 media and placed in the light. Tissue was subcultured onto 110 media following approximately 2 weeks on the second transfer to 105 media. Tissue was allowed to mature on 110 media for approximately 2 weeks before transferring to fresh 110 for a third time; at this point, the cultures were transferred to 110 media contained in PHYTATRAYS™ (plant cell culture vessel). Tissue was allowed to green and further develop for 2-3 more weeks before transplanting the plantlets to soil. Plant were allowed to mature into fertile, transgenic maize plants. In other embodiments, fragments of tissue were transferred onto 211AF media, and other transfer schemes and incubations were employed for continued growth and maintenance prior to subculturing for regeneration into plants.

Following inoculation of BC3F3 immature maize embryos with *Agrobacterium* transformed to contain plasmid pMON61334, transformants and selections were carried out using kanamycin selection. In one embodiment, embryos were transferred from ½ MSPL with 200 µM acetosyringone co-culture media to fresh 600QQ media (0.5×MS salts; 1×MS vitamins; 0.5 mg/L thiamine HCl; 0.115 g/L proline; 10 g/L glucose; 20 g/L sucrose; 3 mg/L 2,4-D; pH to 5.2; supplemented with 20 µM silver thiosulphate; 200 µM acetosyringone and solidified with 5.5 g low melt agarose). Following a 1 day incubation on 600QQ, the embryos were transferred to 142QQR (1×MS salts; 1×MS Fromm; 2 mg/L 2,4-D; 1.36 g/L I-proline; 30 g/L sucrose; pH to 5.6; supplemented with 500 mg/L carbenicillin; 100 mg/L casamino acids and 20 µM silver thiosulphate and solidified with 2.5 g/L phytagel). Following a five day delay on 142QQR, tissue was transferred to fresh 142QQR supplemented with 50 mg/L kanamycin. Tissue was incubated on this media for approximately 2 weeks followed by a transfer to 142EEQQR (media 142QQR supplemented with 100 mg/L kanamycin). After approximately 2 weeks, tissue was transferred to fresh 142EEQQR for about an additional 2 weeks. Tissue was transferred 4 times at approximately 2 week intervals to media 142FQQR (media 142QQR supplemented with 100 mg/L kanamycin). Healthy, friable callus was selected for regeneration on media 105 and 110 following a scheme as described in this example, followed by transplantation to soil and maturation into fertile, transgenic maize plants.

Following inoculation of BC3F4 or BC3F5 immature maize embryos with *Agrobacterium* transformed to contain plasmid pMON61332 or pMON70801, transformants and selections were carried out using glyphosate selection. In one embodiment, embryos were transferred from ½ MSPL with 200 µM acetosyringone co-culture media to fresh 600QQ media (prepared with either 20 µM silver thiosulphate or 20 µM silver nitrate) for 1 day followed by approximately 5 days on media 142QQR (prepared with either 20 µM silver thiosulphate or 20 µM silver nitrate). Tissue was then transferred to fresh 143QQRU (1×MS salts; 1×MS Fromm; 2 mg/L 2,4-D; 1.36 g/L I-proline; 30 g/L sucrose; pH to 5.6; supplemented with 500 mg/L carbenicillin; 0.5 mM glyphosate and either 20 µM silver thiosulphate or 20 µM silver nitrate, and solidified with 2.5 g/L phytagel). After approximately 2 weeks, tissues were transferred to 143JQQR (media 143QQRU except the glyphosate concentration was increased to 1 mM). Tissue was transferred 5 more times at approximately 2 week intervals to media 143KQQR (media 143JQQR except the glyphosate concentration was increased to 3 mM). Healthy, friable callus was selected for regeneration on media 217 and 127 following a scheme as described in this example, followed by transplantation to soil and maturation into fertile, transgenic maize plants. In another embodiment, healthy, friable callus was selected for regeneration on media 105 and 110 following a scheme as described in this example, followed by transplantation to soil and maturation into fertile, transgenic maize plants.

One skilled in the art would realize that the incubation time on any given media at any point in time in the selection and regeneration process will vary in accordance with the amount of tissue, health of tissue and development of tissue. One of skill would also know that many types of media, selection, transfer and incubation regimes would allow for the regeneration of transformed plants, regardless of the type of selection agent employed.

Example 6

Hybrid and Inbred Yield Trials and Field Characteristics

Research yield trials are a means of measuring the yield and other agronomic characteristics of a desired crop plant in a statistical manner (see for example Little and Hills, 1978). In these trials, the desired lines are grown in a number of locations and in several replicates at each location to determine the overall performance of the line A. Hybrid Yield Trials Yield trials were carried out on hybrid lines produced with selected BC3F3 lines. Four different lead lines (178-74, 178-187, 178-270 and 125-2) were crossed to two different tester lines (LH82 and MBZA) for generation of the hybrids. Hybrids were also produced using the parental line FBLL crossed with either LH82 or MBZA were also prepared for testing. Eleven different field locations were used as growing sites and three replications of each hybrid were grown per location. Each plot of each replicate contained 2 rows of each line, approximately 35 plants per row. The sites were located in Ohio, Illinois, Iowa, South Dakota and Indiana. The relative maturity (RM) at the sites varied from 105 to 115 days, although testing could occur in areas with RMs of about 100 to 125, about 90 to 125, about 80 to 125 or about 75 to 125. Relative maturity is a term known in the art that defines the length of the growing season for the area based upon day length, latitude and elevation.

The mean yields for the hybrids are reported in Table 14. The data indicate that the yield for the 178 hybrid lines was line and tester dependent; in some instances, the yield difference was not significantly different while in other crosses, the yield was significantly different at the $P=0.05$ level relative to the control hybrids of LH82×FBLL or MBZA×FBLL. Yield for the hybrids made with the 125-2 line was significantly different from the controls crosses at the $P=0.01$ level. However, the yield of the hybrid FBLL×Hi-II BC3F3 by LH82 or MBZA lines used in this experiment (ranging from 161.03 to 175.51 bushels per acre) are significantly above average commercial yield levels of approximately 137 to 138 bushels per acre for hybrid corn in 2000 and 2001 (USDA Crop Production 2001 Summary, Cr Pr 2-1 (02), 2002). Similar results for other characteristics were observed and are listed in Table 13.

A number of agronomic characteristics were measured in addition to yield including kernel moisture, growing degree units, silking, plant height and ear height. These terms and means of measuring are known to those of skill in the art. Kernel moisture was a measure of the amount of water in a fully mature kernel (approximately 55 days post pollination). Growing degree units (GDU) was a measure of the units of heat required for proper flowering of the growing plant. GDU was a cumulative measurement for which recording started at the plant date and was a measure of the difference between the high and low temperatures for the day. GDUs were determined for the point in time when approximately 50% of the field plants were showing silks and then again when pollen shed (anthesis) occurred. Silking was a measure of the time from the planting date until approximately 50% of the field plants were showing silks. Plant height was measured in inches and recorded the distance from the soil line to the collar (the base) of the flag leaf (top leaf). Typically, one representative plant per plot was measured. Ear height was a measure of the distance from the soil line to the ear node, measured in inches. Typically, one representative plant per plot was measured Greensnap is recorded as the number of plants in a given plot which are broken or snapped in response to a high wind event. Stay green is a measure of the green tissue in a plot at any given time and is relative for the plants in the test at the time. It is common to measure staygreen when a plot is 50% green/50% brown and determining which plants are relatively more green or relatively more brown at the time of comparison.

TABLE 13

Mean results of yield and other characteristics of hybrid lines made by crossing FBLL×Hi-II BC3F3 to tester lines LH82 or MBZA.

| Tester | Line | Yield | Moisture | GDU | Silk | Plant height | Ear height |
|--------|------|-------|----------|-----|------|--------------|------------|
| LH82 | 178-74 | 171.03* | 18.53** | 1320 | 1328 | 78.48 | 34.76** |
| LH82 | 178-187 | 171.59* | 18.72** | 1304** | 1312** | 80.57 | 36.19** |
| LH82 | 178-270 | 175.51 | 18.37* | 1311 | 1315* | 78.57 | 35.19** |
| LH82 | 125-2 | 167.31** | 18.58** | 1316 | 1339 | 76.95 | 32.90** |
| LH82 | FBLL | 181.28 | 17.94 | 1324 | 1337 | 78.76 | 39.57 |
| MBZA | 178-74 | 167.52 | 16.43 | 1362 | 1371 | 82.33 | 41.00 |
| MBZA | 178-187 | 170.80 | 16.28* | 1342 | 1361 | 84.15 | 42.48 |
| MBZA | 178-270 | 167.46 | 16.58 | 1352 | 1371 | 82.05 | 40.19 |
| MBZA | 125-2 | 161.03** | 16.65 | 1355 | 1369 | 79.81** | 39.05* |
| MBZA | FBLL | 172.61 | 16.71 | 1353 | 1369 | 83.19 | 42.19 |

*= significantly different from control FBLL cross at the 0.05 level
**= significantly different from control FBLL cross at the 0.01 level B. Inbred Yield Trials Yield trials are carried out on inbred lines using the parental lines Hi-II, A188, FBLL and the various FBLL×Hi-II BC3F6 test lines. The parental and test lines are grown in several different field locations, preferably 10 to 12 locations and are grown in replicates per field, preferably at least 3 replicates per field. The sites are located in several states and the relative maturity may range from about 120 to 125, about 110 to 125, about 100 to 125, about 90 to 125, about 80 to 125 or about 75 to 125, preferably ranging from about 100 to 120 and most preferable from about 105 to 115 days. The results for the yield for the parental inbred lines are calculated and compared to the yield of the FBLL×Hi-II inbred lines showing enhanced transformability.

C. Field Characteristics

In-bred lines of the parental lines FBLL and A188, as well as the lines bred for enhanced transformability, 178-74-25 and 178-187-20, were field grown for observation. It is important to note that the growing conditions that season were drier than normal for that area; all plants were grown under the same field conditions, hand-pollinated, and all experienced the same stresses. Listed in Table 14 are observations for a number of parameters useful for identifying FBLL MAB lines 178-74-25 and 178-187-20, including comparative measures for parental lines FBLL and Hi-II. Measurements were take using 5 plants, 5 ears of each line, or 5 kernels from each ear and an average and standard deviation are reported.

Ear-Cob Color: The color of the cob, scored as white, pink, red, or brown.
Ear-Cob Diameter: The average diameter of the cob measured at the midpoint.
Ear-Day to First Silk: The number of days after planting in which the silks are first visible.
Ear-Diameter: The average diameter of the ear at its midpoint.
Ear-Dry Husk Color: The color of the husks at harvest scored as buff, red, or purple.
Ear-Fresh Husk Color: The color of the husks 1 to 2 weeks after pollination scored as green, red, or purple.
Ear-Length: The average length of the ear.
Ear-Number Per Stalk: The average number of ears per plant.
Ear-Silk Color: The color of the silk observed 2 to 3 days after silk emergence scored as green-yellow, yellow, pink, red, or purple.
Kernel-Cap Color: The color of the kernel cap observed at dry stage, scored as white, lemon-yellow, yellow or orange.
Kernel-Endosperm Color: The color of the endosperm scored as white, pale yellow, or yellow.
Kernel-Endosperm Type: The type of endosperm scored as normal, waxy, or opaque.
Kernel-Length: The average distance from the cap of the kernel to the pedicel. Five kernels per ear were measured and the average for the 5 kernels is reported for each ear. The Average and Standard Deviation represents all kernels counted for all ears of that genotype.
Kernel-Number Per Row: The average number of kernels in a single row.
Kernel-Row Number: The average number of rows of kernels on a single ear.
Kernel-Side Color: The color of the kernel side observed at the dry stage, scored as white, pale yellow, yellow, orange, red, or brown.
Kernel-Thickness: The distance across the narrow side of the kernel. Five kernels per ear were measured and the average for the 5 kernels is reported for each ear. The Average and Standard Deviation represents all kernels counted for all ears of that genotype.
Kernel-Type: The type of kernel scored as dent, flint, or intermediate.
Kernel-Weight: The average weight of a predetermined number of kernels.
Kernel-Width: The distance across the flat side of the kernel. Five kernels per ear were measured and the average for the 5 kernels is reported for each ear. The Average and Standard Deviation represents all kernels counted for all ears of that genotype.
Leaf-Length: The average length of the primary ear leaf.
Leaf-Longitudinal Creases: A rating of the number of longitudinal creases on the leaf surface 1 to 2 weeks after pollination. Creases are scored as absent, few, or many.
Leaf-Marginal: Waves: A rating of the waviness of the leaf margin 1 to 2 weeks after pollination. Rated as none, few, or many.
Leaf-Sheath Anthocyanin: A rating of the level of anthocyanin in the leaf sheath 1 to 2 weeks after pollination, scored as absent, basal-weak, basal-strong, weak or strong.
Leaf-Width: The average width of the primary ear leaf measured at its widest point.
Stalk-Anthocyanin: A rating of the amount of anthocyanin pigmentation in the stalk. The stalk is rated 1 to 2 weeks after pollination as absent, basal-weak, basal-strong, weak, or strong.
Stalk-Brace Root Color: The color of the brace roots observed 1 to 2 weeks after pollination as green, red, or purple.
Stalk-Ear Height: The average height of the ear measured from the ground to the point of attachment of the ear shank of the top developed ear to the stalk.

Stalk-Internode Direction: The direction of the stalk internode observed after pollination as straight or zigzag.
Stalk-Internode Length: The average length of the internode above the primary ear.
Stalk-Nodes With Brace Roots: The average number of nodes having brace roots per plant.
Tassel-Anther Color: The color of the anthers at 50 percent pollen shed scored as green-yellow, yellow, pink, red, or purple.
Tassel-Attitude: The attitude of the tassel after pollination scored as open or compact.
Tassel-Branch Number: The average number of primary tassel branches.
Tassel-Days to 50% Shed: The number of days from the planting date when 50% of the pollen has been shed.
Tassel-Glume Color: The color of the glumes at 50 percent shed scored as green, red, or purple.
Tassel-Length: The length of the tassel measured from the base of the bottom tassel branch to the tassel tip.
Tassel-Peduncle Length: The average length of the tassel peduncle, measured from the base of the flag leaf to the base of the bottom tassel branch.
Tassel-Spike Length: The length of the spike measured from the base of the top tassel branch to the tassel tip.

TABLE 14

Comparison of characteristics between the FBLL MAB lines and parental lines.

| Tissue | Characteristic | Unit of measurement | Data Collection | 178-74-25 | 178-187-20 | FBLL | Hi-II |
|---|---|---|---|---|---|---|---|
| STALK | Internode Length | cm; avg above primary ear | Pre-pollination | 12.4 | 11.8 | 13.0 | 13.4 |
| | | | | 12.0 | 12.0 | 12.5 | 13.0 |
| | | | | 12.5 | 12.5 | 13.0 | 14.0 |
| | | | | 12.0 | 12.0 | 13.0 | 14.3 |
| | | | | 12.1 | 12.6 | 13.5 | 14.1 |
| | | | Average | 12.2 | 12.2 | 13.0 | 13.8 |
| | | | Std. Deviation | 0.2 | 0.3 | 0.4 | 0.5 |
| STALK | Ear Height | cm; avg from ground to attach point of top ear | Pre-pollination | 43.2 | 26.0 | 59.7 | 34.9 |
| | | | | 39.4 | 29.2 | 40.0 | 34.3 |
| | | | | 41.3 | 35.6 | 50.8 | 44.4 |
| | | | | 34.3 | 29.2 | 50.8 | 35.6 |
| | | | | 34.3 | 30.5 | 50.8 | 42.5 |
| | | | Average | 38.5 | 30.1 | 50.4 | 38.3 |
| | | | Std. Deviation | 4.1 | 3.5 | 7.0 | 4.7 |
| LEAF | Length | cm; primary ear leaf | Pre-pollination | 54.6 | 45.7 | 57.1 | 62.2 |
| | | | | 59.0 | 54.6 | 61.0 | 55.2 |
| | | | | 57.1 | 48.9 | 64.8 | 66.0 |
| | | | | 51.4 | 53.3 | 55.9 | 62.9 |
| | | | | 54.6 | 48.9 | 63.5 | 63.5 |
| | | | Average | 55.3 | 50.3 | 60.5 | 62.0 |
| | | | Std. Deviation | 2.9 | 3.6 | 3.9 | 4.0 |
| LEAF | Width | cm; primary ear leaf widest point | Pre-pollination | 7.7 | 5.5 | 7.3 | 8.6 |
| | | | | 8.5 | 5.5 | 7.2 | 6.5 |
| | | | | 7.9 | 6.0 | 7.4 | 9.0 |
| | | | | 6.7 | 5.9 | 7.2 | 7.5 |
| | | | | 7.0 | 5.9 | 7.8 | 8.0 |
| | | | Average | 7.6 | 5.8 | 7.4 | 7.9 |
| | | | Std. Deviation | 0.7 | 0.2 | 0.2 | 1.0 |
| TASSEL | Attitude | Open (o), compact (c) | Pollination | c | c | c | o |
| | | | | c | c | c | o |
| | | | | c | c | c | o |
| TASSEL | Attitude | Open (o), compact (c) | Pollination | c | c | c | o |
| | | | | c | c | c | o |
| TASSEL | Length | cm; base of bottom talled branch to tip | Pollination | 34.0 | 35.0 | 31.5 | 36.0 |
| | | | | 33.0 | 32.3 | 30.3 | 31.0 |
| | | | | 31.5 | 37.8 | 29.7 | 42.0 |
| | | | | 37.8 | 35.6 | 32.0 | 33.8 |
| | | | | 32.5 | 36.5 | 33.8 | 35.4 |
| | | | Average | 33.8 | 35.4 | 31.5 | 35.6 |
| | | | Std. Deviation | 2.4 | 2.0 | 1.6 | 4.0 |

TABLE 14-continued

Comparison of characteristics between the FBLL MAB lines and parental lines.

| Tissue | Characteristic | Unit of measurement | Data Collection | 178-74-25 | 178-187-20 | FBLL | Hi-II |
|---|---|---|---|---|---|---|---|
| TASSEL | Spike Length | cm; base of the top tassel branch to the tassel tip | Pollination | 19.5 | 17.4 | 15.7 | 26.0 |
| | | | | 16.3 | 17.2 | 15.7 | 22.7 |
| | | | | 17.5 | 17.8 | 14.2 | 26.8 |
| | | | | 19.6 | 17.5 | 14.4 | 25.0 |
| | | | | 15.3 | 17.6 | 18.2 | 25.0 |
| | | | Average | 17.6 | 17.5 | 15.6 | 25.1 |
| | | | Std. Deviation | 1.9 | 0.2 | 1.6 | 1.5 |
| TASSEL | Peduncle Length | cm; base of flag leaf to base of the bottom tassel branch | Pollination | 11.5 | 12.0 | 10.8 | 8.7 |
| | | | | 9.3 | 11.0 | 9.5 | 7.7 |
| | | | | 10.0 | 15.4 | 9.1 | — |
| | | | | 15.5 | 12.4 | 10.7 | 12.2 |
| | | | | 12.5 | 12.1 | 10.5 | 9.7 |
| | | | Average | 11.8 | 12.6 | 10.1 | 9.6 |
| | | | Std. Deviation | 2.4 | 1.7 | 0.8 | 1.9 |
| TASSEL | Branch Number | primary tassel branched | Pollination | 3.0 | 5.0 | 6.0 | 21.0 |
| | | | | 4.0 | 4.0 | 4.0 | 16.0 |
| | | | | 4.0 | 4.0 | 5.0 | 19.0 |
| | | | | 5.0 | 4.0 | 5.0 | 18.0 |
| | | | Average | 4.0 | 4.3 | 5.0 | 18.5 |
| | | | Std. Deviation | 0.8 | 0.5 | 0.8 | 2.1 |
| TASSEL | Anther Color | green-yellow, yellow, pink, red, purple | Pollination | yellow | yellow | pink | yellow |
| | | | | yellow | yellow | pink | yellow |
| | | | | yellow | yellow | pink | yellow |
| | | | | yellow | yellow | pink | yellow |
| | | | | yellow | yellow | pink | yellow |
| TASSEL | Glume Color | green, red, purple | Pollination | red | red | red | red |
| | | | | red | red | red | red |
| | | | | red | red | red | red |
| | | | | red | red | red | red |
| | | | | red | red | red | red |
| TASSEL | Days to 50% shed | from planting | Pollination | 78.0 | 80.0 | 82.0 | 79.0 |
| EAR | Day to first silk | from planting | Pollination | 79.0 | 81.0 | 83.0 | 80.0 |
| EAR | Silk Color | green/yellow, yellow, pink, red, purple | Pollination | pink | pink | red | green |
| | | | | pink | pink | red | green |
| | | | | pink | pink | red | green |
| | | | | pink | pink | red | green |
| | | | | pink | pink | red | green |
| EAR | Husk Color Fresh | green, red, purple | Pollination | green | green | green | green |
| | | | | green | green | green | green |
| | | | | green | green | green | green |
| | | | | green | green | green | green |
| | | | | green | green | green | green |
| EAR | Length | cm; avg length of ear | Dried ear | 127.17 | 135.83 | 111.77 | 149.80 |
| | | | | 142.92 | 123.35 | 134.59 | 130.32 |
| | | | | 134.12 | 103.07 | 129.79 | 137.65 |
| | | | | 145.44 | 96.48 | 109.19 | 155.14 |
| EAR | Length | cm; avg length of ear | Dried ear | 95.89 | 86.39 | 126.00 | not measured* |
| | | | Average | 129.11 | 109.02 | 122.27 | 143.23 |
| | | | Std. Deviation | 19.94 | 20.18 | 11.22 | 11.30 |
| EAR | Diameter | cm; at midpoint w/kernels | Dried ear | 35.17 | 32.21 | 41.16 | 36.84 |
| | | | | 33.00 | 36.84 | 37.87 | 41.79 |
| | | | | 31.72 | 35.01 | 40.20 | 38.54 |

TABLE 14-continued

Comparison of characteristics between the FBLL MAB lines and parental lines.

| Tissue | Characteristic | Unit of measurement | Data Collection | 178-74-25 | 178-187-20 | FBLL | Hi-II |
|---|---|---|---|---|---|---|---|
| | | | | 37.19 | 37.38 | 40.24 | 39.58 |
| | | | | 35.91 | 38.22 | 41.32 | not measured* |
| | | | Average | 34.60 | 35.93 | 40.16 | 39.19 |
| | | | Std. Deviation | 2.21 | 2.39 | 1.38 | 2.07 |
| EAR | Husk Color Dry | buff, red, purple | Dried ear | Buff | Buff | Buff | Buff |
| | | | | Buff | Buff | Buff | Buff |
| | | | | Buff | Buff | Buff | Buff |
| | | | | Buff | Buff | Buff | Buff |
| | | | | Buff | Buff | Buff | Buff |
| EAR | Cob Diameter | cm; shelled, midpoint | Dried ear | 23.54 | 26.92 | 25.98 | 24.42 |
| | | | | 23.74 | 26.68 | 22.42 | 26.20 |
| | | | | 25.13 | 26.83 | 25.75 | 25.03 |
| | | | | 26.64 | 24.11 | 24.76 | 24.29 |
| | | | | 21.41 | 25.76 | 24.93 | not measured* |
| | | | Average | 24.09 | 26.06 | 24.77 | 24.99 |
| | | | Std. Deviation | 1.95 | 1.18 | 1.41 | 0.87 |
| EAR | Cob Color | white, pink, red, brown | Dried ear | White | White | Red | White |
| | | | | White | White | Red | White |
| | | | | White | White | Red | White |
| | | | | White | White | Red | White |
| | | | | White | White | Red | not measured* |
| KERNEL | Row Number | avg number of rows | Dried ear | 14.0 | 14.0 | 14.0 | 14.0 |
| | | | | 14.0 | 12.0 | 16.0 | 16.0 |
| | | | | 12.0 | 14.0 | 14.0 | 14.0 |
| | | | | 14.0 | 14.0 | 14.0 | 14.0 |
| | | | | 12.0 | 12.0 | 16.0 | not measured* |
| | | | Average | 13.2 | 13.2 | 14.8 | 14.5 |
| | | | Std. Deviation | 1.1 | 1.1 | 1.1 | 1.0 |
| KERNEL | Number Per Row | avg number of K per single row | Dried ear | 26.0 | 13.0 | 14.0 | 18.0 |
| | | | | 26.0 | 22.0 | 20.0 | 24.0 |
| | | | | 20.0 | 8.0 | 19.0 | 24.0 |
| | | | | 16.0 | 10.0 | 20.0 | 20.0 |
| | | | | 17.0 | poor rows | 20.0 | not measured* |
| | | | Average | 21.0 | 13.3 | 18.6 | 21.5 |
| | | | Std. Deviation | 4.8 | 6.2 | 2.6 | 3.0 |
| KERNEL | Type | dent, flint, intermediate | Dried ear | dent | dent | dent | dent |
| | | | | dent | dent | dent | dent |
| | | | | dent | dent | dent | dent |
| | | | | dent | dent | dent | dent |
| | | | | dent | dent | dent | not measured* |
| KERNEL | Cap Color | white, yellow (y), lemon-yellow (ly), orange | Dried ear | lemon-yellow | lemon-yellow | mix of y and ly | white |
| | | | | lemon-yellow | lemon-yellow | mix of y and ly | white |
| | | | | lemon-yellow | lemon-yellow | mix of y and ly | white |
| | | | | lemon-yellow | lemon-yellow | mix of y and ly | white |
| | | | | lemon-yellow | lemon-yellow | mix of y and ly | not measured* |

TABLE 14-continued

Comparison of characteristics between the FBLL MAB lines and parental lines.

| Tissue | Characteristic | Unit of measurement | Data Collection | 178-74-25 | 178-187-20 | FBLL | Hi-II |
|---|---|---|---|---|---|---|---|
| KERNEL | Side Color | white, yellow, pale-yellow, orange, red, brown | Dried ear | pale yellow | pale yellow | yellow | pale yellow |
| | | | | pale yellow | pale yellow | yellow | pale yellow |
| | | | | pale yellow | pale yellow | yellow | pale yellow |
| | | | | pale yellow | pale yellow | yellow | pale yellow |
| | | | | pale yellow | pale yellow | yellow | not measured* |
| KERNEL | Length (depth) | mm; cap to pedicel^ | Dried ear | 8.81 | 10.24 | 11.21 | 10.29 |
| | | | | 9.40 | 8.58 | 10.66 | 10.35 |
| | | | | 9.06 | 9.79 | 11.01 | 10.97 |
| | | | | 9.75 | 9.28 | 11.58 | 10.78 |
| | | | | 8.97 | 9.09 | 10.47 | not measured* |
| | | | Average^^ | 9.20 | 9.40 | 10.99 | 10.59 |
| | | | Std. Deviation^^ | 0.50 | 0.72 | 0.53 | 0.45 |
| KERNEL | Width | mm; across flat side^ | Dried ear | 6.62 | 7.28 | 7.62 | 7.87 |
| | | | | 7.05 | 6.24 | 7.20 | 7.66 |
| | | | | 7.10 | 7.99 | 7.17 | 7.27 |
| | | | | 7.49 | 8.43 | 7.36 | 8.18 |
| | | | | 8.46 | 7.22 | 6.94 | not measured* |
| | | | Average^^ | 7.35 | 7.43 | 7.26 | 7.74 |
| | | | Std. Deviation^^ | 0.70 | 0.85 | 0.43 | 0.65 |
| KERNEL | Thickness | mm; narrow side^ | Dried ear | 4.08 | 5.66 | 4.16 | 4.11 |
| | | | | 4.90 | 4.19 | 4.63 | 5.43 |
| | | | | 5.09 | 6.17 | 4.66 | 5.13 |
| | | | | 4.40 | 5.55 | 4.08 | 4.51 |
| | | | | 6.49 | 5.17 | 4.55 | not measured* |
| | | | Average^^ | 4.99 | 5.35 | 4.42 | 4.80 |
| | | | Std. Deviation^^ | 0.91 | 0.90 | 0.51 | 0.61 |
| KERNEL | Weight of 50K | grams | Dried ear | 9.8 | 13.9 | 13.3 | 11.0 |
| | | | | 15.5 | 6.4 | 12.3 | 14.2 |
| | | | | 9.2 | 16.6 | 12.5 | 16.0 |
| | | | | 10.1 | 17.2# | 14.2 | 13.9 |
| | | | | 16.6 | 12.4## | 11.2 | not measured* |
| | | | Average | 12.2 | 13.3 | 12.7 | 13.8 |
| | | | Std. Deviation | 3.5 | 4.3 | 1.1 | 2.1 |
| KERNEL | Endosperm Type | normal, waxy, opaque | Dried ear | normal | normal | normal | normal |
| | | | | normal | normal | normal | normal |
| | | | | normal | normal | normal | normal |
| | | | | normal | normal | normal | normal |
| | | | | normal | normal | normal | not measured* |
| KERNEL | Endosperm Color | white, yellow, pale-yellow | Dried ear | pale yellow | pale yellow | yellow | white |
| | | | | pale yellow | pale yellow | yellow | white |
| | | | | pale yellow | pale yellow | yellow | white |
| | | | | pale yellow | pale yellow | yellow | white |
| | | | | pale yellow | pale yellow | yellow | not measured* |
| STALK | Anthocyanin | absent, basal-weak, basal-strong, weak, strong | 1-2 weeks post poll | basal-weak | absent | basal-weak | basal-weak |
| | | | | basal-weak | basal-weak | basal-weak | basal-weak |
| | | | | basal- | basal- | basal- | basal- |

TABLE 14-continued

Comparison of characteristics between the FBLL MAB lines and parental lines.

| Tissue | Characteristic | Unit of measurement | Data Collection | 178-74-25 | 178-187-20 | FBLL | Hi-II |
|---|---|---|---|---|---|---|---|
| | | | | weak | weak | weak | weak |
| | | | | basal-weak | absent | basal-weak | basal-weak |
| | | | | basal-weak | basal-weak | basal-weak | absent |
| STALK | Brace Root Color | green, red, purple | 1-2 weeks post poll | red | red | purple | purple |
| | | | | red | red | purple | purple |
| | | | | red | red | purple | purple |
| | | | | red | red | purple | purple |
| STALK | Nodes With Brace Roots | number of nodes with brace roots | 1-2 weeks post poll | 3.0 | 2.0 | 3.0 | 3.0 |
| | | | | 3.0 | 2.0 | 3.0 | 2.0 |
| | | | | 3.0 | 2.0 | 3.0 | 3.0 |
| | | | | 2.0 | 3.0 | 3.0 | 3.0 |
| | | | | 2.0 | 2.0 | 3.0 | 2.0 |
| | | | Average | 2.6 | 2.2 | 3.0 | 2.6 |
| | | | Std. Deviation | 0.5 | 0.4 | 0.0 | 0.5 |
| STALK | Internode Direction | straight, zigzag | 1-2 weeks post poll | straight | straight | straight | straight |
| | | | | straight | straight | straight | straight |
| | | | | straight | straight | straight | straight |
| | | | | straight | straight | straight | straight |
| | | | | straight | straight | straight | straight |
| LEAF | Sheath Anthocyanin | absent, basal-weak, basal-strong, weak, strong | 1-2 weeks post poll | basal-weak | basal-weak | basal-weak | basal-weak |
| | | | | basal-weak | basal-weak | basal-weak | basal-weak |
| | | | | basal-weak | basal-weak | basal-weak | basal-weak |
| | | | | basal-weak | basal-weak | basal-weak | basal-weak |
| | | | | basal-weak | basal-weak | basal-weak | basal-weak |
| LEAF | Marginal Waves | none, few, many | 1-2 weeks post poll | few | few | few | few |
| | | | | few | few | few | few |
| | | | | few | few | few | few |
| | | | | few | few | few | few |
| | | | | few | few | few | few |
| LEAF | Longitudinal Creases | absent, few, many | 1-2 weeks post poll | few | few | few | absent |
| | | | | few | few | few | few |
| | | | | few | few | few | few |
| | | | | few | few | few | few |
| | | | | few | few | few | few |
| EAR | Number Per Stalk | avg number per plant | 1-2 weeks post poll | 1.0 | 1.0 | 2.0 | 1.0 |
| | | | | 1.0 | 1.0 | 1.0 | 1.0 |
| | | | | 1.0 | 1.0 | 1.0 | 1.0 |
| | | | | 1.0 | 1.0 | 1.0 | 1.0 |
| | | | | 1.0 | 1.0 | 1.0 | 1.0 |
| | | | Average | 1.0 | 1.0 | 1.2 | 1.0 |
| | | | Std. Deviation | 0.0 | 0.0 | 0.4 | 0.0 |

*ear was too underdeveloped to measure

^the 4 or 5 values represent an average of 5 kernels per ear reported per ear

^^average represents all 20 or 25 kernels measured extrapolated from 48K extrapolated from 35K

Example 7

Maintenance of FBLL×Hi-II Lines

Following the introgression of a desired QTL, such as enhanced transformability, into an elite or any other desired line, it is then necessary to maintain the QTL in the selectively bred germplasm.

Maintenance of a desired line may be achieved by self pollinations, sib pollinations or a combination of sib and self pollinations.

Line maintenance for the Hi-II×FBLL MAB BC3F5 lines was carried out by self pollinations. Where self pollinations were not possible, sib pollinations were carried out.

Example 8

Introgression of Transgenes into Elite Varieties

Backcrossing can be used to improve a starting plant. Backcrossing transfers a specific desirable trait from one source to an inbred or other plant that lacks that trait. This can be accomplished, for example, by first crossing a superior inbred (A) (recurrent parent) to a donor inbred (non-recurrent parent), which carries the appropriate gene(s) for the trait in question, for example, a construct prepared in accordance with the current invention. The progeny of this cross first are selected in the resultant progeny for the desired trait to be transferred from the non-recurrent parent, then the selected progeny are mated back to the superior recurrent parent (A). After five or more backcross generations with selection for the desired trait, the progeny are hemizygous for loci controlling the characteristic being transferred, but are like the superior parent for most or almost all other genes. The last backcross generation would be selfed to give progeny which are pure breeding for the gene(s) being transferred, i.e. one or more transformation events.

Therefore, through a series a breeding manipulations, a selected transgene may be moved from one line into an entirely different line without the need for further recombinant manipulation. Transgenes are valuable in that they typically behave genetically as any other gene and can be manipulated by breeding techniques in a manner identical to any other corn gene. Therefore, one may produce inbred plants which are true breeding for one or more transgenes. By crossing different inbred plants, one may produce a large number of different hybrids with different combinations of transgenes. In this way, plants may be produced which have the desirable agronomic properties frequently associated with hybrids ("hybrid vigor"), as well as the desirable characteristics imparted by one or more transgene(s).

Example 9

Utilization of Transgenic Crops Produced from Lines with Enhanced Transformability The ultimate goal in plant transformation is to produce plants which are useful to man. In this respect, transgenic plants created in accordance with the current invention may be used for virtually any purpose deemed of value to the grower or to the consumer. For example, one may wish to harvest seed from transgenic plants. This seed may in turn be used for a wide variety of purposes. The seed may be sold to farmers for planting in the field or may be directly used as food, either for animals or humans. Alternatively, products may be made from the seed itself. Examples of products which may be made from the seed include, oil, starch, animal or human food, pharmaceuticals, and various industrial products. The food uses of maize, in addition to human consumption of maize kernels, include both products of dry- and wet-milling industries. The principal products of maize dry milling are grits, meal and flour. The maize wet-milling industry can provide maize starch, maize syrups, and dextrose for food use. Maize oil is recovered from maize germ, which is a by-product of both dry- and wet-milling industries.

Maize, including both grain and non-grain portions of the plant, also is used extensively as livestock feed, primarily for beef cattle, dairy cattle, hogs, and poultry. Industrial uses of maize include production of ethanol, maize starch in the wet-milling industry and maize flour in the dry-milling industry. The industrial applications of maize starch and flour are based on functional properties, such as viscosity, film formation, adhesive properties, and ability to suspend particles. The maize starch and flour have application in the paper and textile industries. Other industrial uses include applications in adhesives, building materials, foundry binders, laundry starches, explosives, oil-well muds, and other mining applications. Plant parts other than the grain of maize also are used in industry, for example, stalks and husks are made into paper and wallboard and cobs are used for fuel and to make charcoal. Other means for utilizing plants, such as those that may be made with the current invention, have been well known since the dawn of agriculture and will be known to those of skill in the art in light of the instant disclosure. Specific methods for crop utilization may be found in, for example, Sprague and Dudley (1988), and Watson and Ramstad (1987).

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the methods described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

An et al., *Plant Molecular Biology Manual* A3:1-19, 1998.
Armstrong and Green, *Planta*, 164:207-214, 1985.
Armstrong and Phillips, *Crop Science*, 28:363-369, 1988.
Armstrong et al., *Maize Gen. Coop. Newsletter*, March 1, (65):92-93, 1991.
Armstrong et al., *Theor. Appl. Genet.*, 84:755-762, 1992.
Armstrong et al., *Crop Science*, 35:550-557, 1995.
Arús and Moreno-González, *Plant Breeding*, Hayward, Bosemark, Romagosa (eds.) Chapman & Hall, London, pp. 314-331, 1993.
Ben Amer et al., *Plant Breeding*, 114:84-85, 1995.
Ben Amer et al., *Theor. Appl. Genet.*, 94:1047-1052, 1997.
Bhattramakki et al., *Maize Genetics Coop. Newsletter*, 74:54, 2000.
Bregitzer and Campbell, *Crop Science*, 41:173-179, 2001.
Burr et al., *Genetics*, 118:519-526, 1988.

Chilton et al., *Proc. Natl. Acad. Sci. USA*, 71(9):3672-3676, 1974.
Coe, *Maize Genetics Cooperation Newsletter*, 66:127-159, 1992.
Ditta et al., *Proc. Natl. Acad. Sci. USA*, 77:7374-7351, 1980.
Fehr, In: *Theory and Technique*, 1:360-376, 1987.
Gardiner et al., *Genetics*, 134:917-930, 1993.
Hiei et al., *Plant. Mol. Biol.*, 35(1-2):205-218, 1997.
Jansen et al., *Theor. Appl. Genet.*, 91:33-37, 1995.
Jansen and Stam, *Genetics*, 136:1447-1455, 1994.
Jefferson et al., *Proc. Natl. Acad. Sci. USA*, 83(22):8447-8451, 1986.
Jefferson, *Plant Mol. Biol. Rep.*, 5:387-405, 1987.
Koncz et al., *Mol. Gen. Gen.*, 204:383-396, 1986.
Kruglyak and Lander, *Genetics*, 121:139:1421-1428, 1995.
Kwon et al., *Molecules and Cells*, 11(1):64-67, 2001a.
Kwon et al., *Molecules and Cells*, 12(1):103-106, 2001b.
Lander and Botstein, *Genetics*, 121:185-199, 1989.
Lee et al., poster presentation #54, Genetic analysis of totipotency in maize, 44th Annual Maize Genetics Conference, 2002.
Little and Hills, *Agricultural Experimentation: Design and Analysis*, John Wiley and Sons, Inc., 1978.
Lincoln and Lander, *Mapping Genes Controlling Quantitative Traits Using MAPMAKER/QTL*, Whitehead Institute for Biomedical Research, Massachusetts, 1990.
Mano et al., *Breeding Science*, 46:137-142, 1996.
Murigneux et al., *Genome*, 37:970-976, 1994.
Poehlman, *Breeding of Field Crops, Third edition*, AVI Publishing Co., Inc., p 451-507, 1987.
Reiter et al., *Proc. Natl. Acad. Sci. USA*, 89:1477-1481, 1992.
Rogers et al., *Plant Molecular Biology Manual A*2:1-12, 1988.
Schiantarelli et al., *Theor. Appl. Genet.*, 102:335-342, 2001.
Senior and Heun, *Genome*, 36(5):884-889, 1993.
Songstad, *In vitro cell. and dev. Biol: Plant: Journal of the Tissue Culture Association* July/September v. 32(3), 1996.
Sourdille et al., *Euphytica*, 91:21-30, 1996.
Sprague and Dudley, eds., *Corn and Improvement*, 3rd ed., 1988.
Stuber et al., *Genetics*, 132:823-839, 1992.
Taguchi-Shiobara et al., *Theor. Appl. Genet.*, 95:828-833, 1997.
Takeuchi et al., *Crop Sci.*, 40:245-247, 2000.
Taramino and Tingey, *Genome*, 39(2):277-287, 1996.
Tenaillon et al., *Proc. Natl. Acad. Sci. U.S.A.*, 98(16):9161-9166, 2001.
USDA Crop Production 2001 Summary, Cr Pr 2-1 (02), 2002.
Utz and Melchinger, *Biometrics in Plant Breeding*, van Oijen, Jansen (eds.) Proceedings of the Ninth Meeting of the Eucarpia Section Biometrics in Plant Breeding, The Netherlands, pp. 195-204, 1994.
Watson and Ramstad, eds., *Corn: Chemistry and Technology*, 1987.
Weber and Helentjaris, *Genetics*, 121:583-590, 1989.
Weber and Wricke, *Advances in Plant Breeding*, Blackwell, Berlin 16, 1994.
Wen-jun and Forde, *Nucl. Acids. Res.* 17:8385, 1989.
Williams et al., *Nuc, Acids Res*, 18:6531-6535, 1990.
Zeng, *Genetics*, 136:1457-1468, 1994.

What is claimed is:

1. A seed of the corn variety 178-187-20, wherein a sample of said seed has been deposited under ATCC Accession No. PTA-5183.

2. A plant grown from the seed of claim 1.

3. A hybrid corn seed produced by crossing the plant of claim 2 with a second plant.

4. A method of producing a progeny plant derived from the corn variety 178-187-20 comprising the step of crossing a plant of the corn variety 178-187-20 with a second corn plant to produce said progeny plant, wherein a sample of the seed of the corn variety 178-187-20 was deposited under ATCC Accession No. PTA-5183.

5. The method of claim 4, further comprising the steps of:
(a) crossing the progeny plant with itself or with a second plant to produce a seed of a progeny plant of a subsequent generation;
(b) growing a progeny plant of a subsequent generation from said seed and crossing the progeny plant of a subsequent generation with itself or a second plant; and
(c) repeating steps (a) and (b) for at least 1 additional generation with sufficient inbreeding to produce an inbred corn plant derived from the corn variety 178-187-20.

6. The method of claim 5, further defined as comprising selecting a progeny plant for crossing at one or more generations based on the presence of one or more loci mapping to chromosomal bins 1.03 to 1.06, 1.08 to 1.11, 3.05 to 3.07 or 6.02 to 6.04.

* * * * *

```
                      SEQUENCE LISTING

<160> NUMBER OF SEQ ID NOS: 32

<210> SEQ ID NO 1
<211> LENGTH: 21
<212> TYPE: DNA
<213> ORGANISM: Artificial Sequence
<220> FEATURE:
<223> OTHER INFORMATION: Synthetic Primer

<400> SEQUENCE: 1
gtaaaagacg acgacattcc g                                                  21

<210> SEQ ID NO 2
<211> LENGTH: 20
<212> TYPE: DNA
<213> ORGANISM: Artificial Sequence
<220> FEATURE:
<223> OTHER INFORMATION: Synthetic Primer

<400> SEQUENCE: 2
gacgtgcact ccgtttaaca                                                    20

<210> SEQ ID NO 3
<211> LENGTH: 20
<212> TYPE: DNA
<213> ORGANISM: Artificial Sequence
<220> FEATURE:
<223> OTHER INFORMATION: Synthetic Primer

<400> SEQUENCE: 3
ccgactgact cgagctaacc                                                    20

<210> SEQ ID NO 4
```

```
<211> LENGTH: 20
<212> TYPE: DNA
<213> ORGANISM: Artificial Sequence
<220> FEATURE:
<223> OTHER INFORMATION: Synthetic Primer

<400> SEQUENCE: 4
ccgtaacttc caagaaccga                                              20

<210> SEQ ID NO 5
<211> LENGTH: 20
<212> TYPE: DNA
<213> ORGANISM: Artificial Sequence
<220> FEATURE:
<223> OTHER INFORMATION: Synthetic Primer

<400> SEQUENCE: 5
acacaagccg accaaaaaac                                              20

<210> SEQ ID NO 6
<211> LENGTH: 20
<212> TYPE: DNA
<213> ORGANISM: Artificial Sequence
<220> FEATURE:
<223> OTHER INFORMATION: Synthetic Primer

<400> SEQUENCE: 6
gtagtaggaa cgggcgatga                                              20

<210> SEQ ID NO 7
<211> LENGTH: 18
<212> TYPE: DNA
<213> ORGANISM: Artificial Sequence
<220> FEATURE:
<223> OTHER INFORMATION: Synthetic Primer

<400> SEQUENCE: 7
ttcaccgcct cacatgac                                                18

<210> SEQ ID NO 8
<211> LENGTH: 19
<212> TYPE: DNA
<213> ORGANISM: Artificial Sequence
<220> FEATURE:
<223> OTHER INFORMATION: Synthetic Primer

<400> SEQUENCE: 8
gcaacgctag ctagctttg                                               19

<210> SEQ ID NO 9
<211> LENGTH: 20
<212> TYPE: DNA
<213> ORGANISM: Artificial Sequence
<220> FEATURE:
<223> OTHER INFORMATION: Synthetic Primer

<400> SEQUENCE: 9
acagctcttc ttggcatcgt                                              20

<210> SEQ ID NO 10
<211> LENGTH: 20
<212> TYPE: DNA
<213> ORGANISM: Artificial Sequence
<220> FEATURE:
<223> OTHER INFORMATION: Synthetic Primer

<400> SEQUENCE: 10
```

```
gactttgctg gtcagctggt                                              20

<210> SEQ ID NO 11
<211> LENGTH: 20
<212> TYPE: DNA
<213> ORGANISM: Artificial Sequence
<220> FEATURE:
<223> OTHER INFORMATION: Synthetic Primer

<400> SEQUENCE: 11
tctgctcatc cacaacttgc                                              20

<210> SEQ ID NO 12
<211> LENGTH: 20
<212> TYPE: DNA
<213> ORGANISM: Artificial Sequence
<220> FEATURE:
<223> OTHER INFORMATION: Synthetic Primer

<400> SEQUENCE: 12
agaacgtgaa gctgagcgtt                                              20

<210> SEQ ID NO 13
<211> LENGTH: 19
<212> TYPE: DNA
<213> ORGANISM: Artificial Sequence
<220> FEATURE:
<223> OTHER INFORMATION: Synthetic Primer

<400> SEQUENCE: 13
tcctgccccc tttgttttc                                               19

<210> SEQ ID NO 14
<211> LENGTH: 20
<212> TYPE: DNA
<213> ORGANISM: Artificial Sequence
<220> FEATURE:
<223> OTHER INFORMATION: Synthetic Primer

<400> SEQUENCE: 14
cacctctgaa cccctgtgtt                                              20

<210> SEQ ID NO 15
<211> LENGTH: 20
<212> TYPE: DNA
<213> ORGANISM: Artificial Sequence
<220> FEATURE:
<223> OTHER INFORMATION: Synthetic Primer

<400> SEQUENCE: 15
tgcttgcact gtcaggaatc                                              20

<210> SEQ ID NO 16
<211> LENGTH: 20
<212> TYPE: DNA
<213> ORGANISM: Artificial Sequence
<220> FEATURE:
<223> OTHER INFORMATION: Synthetic Primer

<400> SEQUENCE: 16
cagctctgac acaccacaca                                              20

<210> SEQ ID NO 17
<211> LENGTH: 20
<212> TYPE: DNA
<213> ORGANISM: Artificial Sequence
<220> FEATURE:
```

<223> OTHER INFORMATION: Synthetic Primer

<400> SEQUENCE: 17
aatactggac caccaggcac         20

<210> SEQ ID NO 18
<211> LENGTH: 18
<212> TYPE: DNA
<213> ORGANISM: Artificial Sequence
<220> FEATURE:
<223> OTHER INFORMATION: Synthetic Primer

<400> SEQUENCE: 18
cgtgggtcac caggagtc         18

<210> SEQ ID NO 19
<211> LENGTH: 20
<212> TYPE: DNA
<213> ORGANISM: Artificial Sequence
<220> FEATURE:
<223> OTHER INFORMATION: Synthetic Primer

<400> SEQUENCE: 19
aagttggtgg tgccaagaag         20

<210> SEQ ID NO 20
<211> LENGTH: 20
<212> TYPE: DNA
<213> ORGANISM: Artificial Sequence
<220> FEATURE:
<223> OTHER INFORMATION: Synthetic Primer

<400> SEQUENCE: 20
aaaaggtcca cgtgaacagg         20

<210> SEQ ID NO 21
<211> LENGTH: 20
<212> TYPE: DNA
<213> ORGANISM: Artificial Sequence
<220> FEATURE:
<223> OTHER INFORMATION: Synthetic Primer

<400> SEQUENCE: 21
cgaaagtcga tcgagagacc         20

<210> SEQ ID NO 22
<211> LENGTH: 20
<212> TYPE: DNA
<213> ORGANISM: Artificial Sequence
<220> FEATURE:
<223> OTHER INFORMATION: Synthetic Primer

<400> SEQUENCE: 22
cctctcttca ccccttcctt         20

<210> SEQ ID NO 23
<211> LENGTH: 20
<212> TYPE: DNA
<213> ORGANISM: Artificial Sequence
<220> FEATURE:
<223> OTHER INFORMATION: Synthetic Primer

<400> SEQUENCE: 23
aggatcccct agcaaaagga         20

<210> SEQ ID NO 24

```
<211> LENGTH: 20
<212> TYPE: DNA
<213> ORGANISM: Artificial Sequence
<220> FEATURE:
<223> OTHER INFORMATION: Synthetic Primer

<400> SEQUENCE: 24 cccccctagtt cgttgcataa                                              20

<210> SEQ ID NO 25
<211> LENGTH: 20
<212> TYPE: DNA
<213> ORGANISM: Artificial Sequence
<220> FEATURE:
<223> OTHER INFORMATION: Synthetic Primer

<400> SEQUENCE: 25
accgacctaa gctatgggct                                               20

<210> SEQ ID NO 26
<211> LENGTH: 20
<212> TYPE: DNA
<213> ORGANISM: Artificial Sequence
<220> FEATURE:
<223> OTHER INFORMATION: Synthetic Primer

<400> SEQUENCE: 26
ccggttataa acacagccgt                                               20

<210> SEQ ID NO 27
<211> LENGTH: 20
<212> TYPE: DNA
<213> ORGANISM: Artificial Sequence
<220> FEATURE:
<223> OTHER INFORMATION: Synthetic Primer

<400> SEQUENCE: 27
acgggagaac aaaaggaagg                                               20

<210> SEQ ID NO 28
<211> LENGTH: 18
<212> TYPE: DNA
<213> ORGANISM: Artificial Sequence
<220> FEATURE:
<223> OTHER INFORMATION: Synthetic Primer

<400> SEQUENCE: 28 ctctcccctca catccgcc                                                18

<210> SEQ ID NO 29
<211> LENGTH: 18
<212> TYPE: DNA
<213> ORGANISM: Artificial Sequence
<220> FEATURE:
<223> OTHER INFORMATION: Synthetic Primer

<400> SEQUENCE: 29
caggtactac gtgccgtg                                                 18

<210> SEQ ID NO 30
<211> LENGTH: 21
<212> TYPE: DNA
<213> ORGANISM: Artificial Sequence
<220> FEATURE:
<223> OTHER INFORMATION: Synthetic Primer

<400> SEQUENCE: 30
```

-continued

```
ctagagacaa acgaggctag g                                              21

<210> SEQ ID NO 31
<211> LENGTH: 20
<212> TYPE: DNA
<213> ORGANISM: Artificial Sequence
<220> FEATURE:
<223> OTHER INFORMATION: Synthetic Primer

<400> SEQUENCE: 31
tgcttcagcg cattaaactg                                                20

<210> SEQ ID NO 32
<211> LENGTH: 20
<212> TYPE: DNA
<213> ORGANISM: Artificial Sequence
<220> FEATURE:
<223> OTHER INFORMATION: Synthetic Primer

<400> SEQUENCE: 32
tgctcgtgtg agttcctacg                                                20
```